United States Patent
Owen et al.

(10) Patent No.: US 9,802,945 B2
(45) Date of Patent: Oct. 31, 2017

(54) IMIDAZOPYRIDAZINE DERIVATIVES AS MODULATORS OF THE GABAA RECEPTOR ACTIVITY

(71) Applicant: Pfizer Limited, Sandwich, Kent (GB)

(72) Inventors: Robert McKenzie Owen, Great Abington (GB); David Cameron Pryde, Great Abington (GB); Mifune Takeuchi, Sandwich (GB); Christine Anne Louise Watson, Sandwich (GB)

(73) Assignee: Pfizer Limited, Sandwich, Kent (GB)

( * ) Notice: Subject to any disclaimer, the term of this patent is extended or adjusted under 35 U.S.C. 154(b) by 0 days.

(21) Appl. No.: 15/316,552

(22) PCT Filed: Jun. 3, 2015

(86) PCT No.: PCT/IB2015/054200
§ 371 (c)(1),
(2) Date: Dec. 6, 2016

(87) PCT Pub. No.: WO2015/189744
PCT Pub. Date: Dec. 17, 2015

(65) Prior Publication Data
US 2017/0197965 A1    Jul. 13, 2017

Related U.S. Application Data

(60) Provisional application No. 62/011,137, filed on Jun. 12, 2014.

(51) Int. Cl.
C07D 487/04 (2006.01)
A61K 31/496 (2006.01)
A61K 31/5025 (2006.01)

(52) U.S. Cl.
CPC ........ *C07D 487/04* (2013.01); *A61K 31/5025* (2013.01)

(58) Field of Classification Search
None
See application file for complete search history.

(56) References Cited

U.S. PATENT DOCUMENTS 8,952,008 B2 *   2/2015   Omoto ............... A61K 31/5025
                                                            514/248

FOREIGN PATENT DOCUMENTS

WO        0118000       3/2001
WO        2006078891    7/2006

OTHER PUBLICATIONS

International Patent Application PCT/IB2015/054200, filed Jun. 3, 2015, International Search Report and Written Opinion of the International Searching Authority, dated Sep. 3, 2015, 12 pages.
Russell, Michael G.N., et al., "Discovery of Imidazo[1,2-b][1,2,4]triazines as GABAA α2/3 Subtype Selective Agonists for the Treatment of Anxiety", Journal of Medicinal Chemistry, Feb. 1, 2006, pp. 1235-1238, 49(4).

* cited by examiner

*Primary Examiner* — Emily Bernhardt
(74) *Attorney, Agent, or Firm* — Richard V. Zanzalari

(57) ABSTRACT

The present invention relates to imidazopyridazine derivatives. More particularly, it relates to 4-(biphenyl-3-yl)-7H-imidazo[4,5-c]pyridazine derivatives of formula (I):

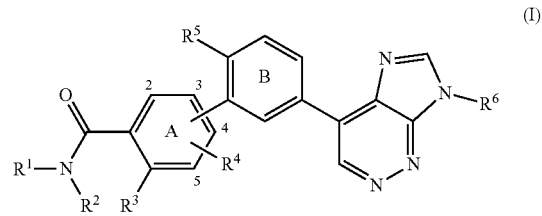

and pharmaceutically acceptable salts thereof, wherein $R^1$, $R^2$, $R^3$, $R^4$, $R^5$ and $R^6$ are as defined in the description. The imidazopyridazine derivatives of the present invention modulate the activity of the $GABA_A$ receptor. They are useful in the treatment of a number of conditions, including pain.

9 Claims, No Drawings

IMIDAZOPYRIDAZINE DERIVATIVES AS MODULATORS OF THE GABAA RECEPTOR ACTIVITY

This application is a national stage application under 35 U.S.C. 371 of PCT/162015/054200, filed on Jun. 3, 2015, which claims the benefit of U.S. Provisional Patent Application No. 62/011,137, filed on Jun. 12, 2014, the disclosures of which are hereby incorporated by reference in their entirety.

FIELD OF THE INVENTION

The present invention relates to imidazopyridazine derivatives. More particularly, it relates to 4-(biphenyl-3-yl)-7H-imidazo[4,5-c]pyridazine derivatives. The imidazopyridazine derivatives of the present invention modulate the activity of the $GABA_A$ receptor. They are useful in the treatment of a number of conditions, including pain.

BACKGROUND

Gamma-aminobutyric acid (GABA) has been identified as a major inhibitory neurotransmitter, and agents that modulate GABAergic neurotransmission are used extensively in the treatment of conditions such as epilepsy, anxiety and depression. Two families of GABA receptor have been described, termed $GABA_A$ and $GABA_B$.

The $GABA_A$ receptor is a member of the ligand-gated ion channel superfamily. The functional receptor generally comprises a number of subunits. At least 16 such subunits have been characterized, including 6 alpha subunits ($\alpha_{1-6}$), 3 beta subunits ($\beta_{1-3}$), 3 gamma subunits ($\gamma_{1-3}$), and delta, epsilon, pi and theta subunits ($\delta, \epsilon, \pi, \theta$). Most $GABA_A$ receptors are made up of 2 alpha, 2 beta and one gamma subunit. Several drug binding sites have been described. These include the binding site for the endogenous ligand (GABA), and allosteric binding sites. Drugs that bind at the allosteric binding sites may be positive allosteric modulators, which increase responsiveness, negative allosteric modulators, which decrease receptor responsiveness, or neutral, which term refers to compounds that bind to the allosteric binding sites without modulating the activity of the receptor. Recent evidence has suggested that $GABA_A$ receptors comprising either the $\alpha_2$ or $\alpha_3$ subunit (herein termed $GABA_A$ $\alpha_{2/3}$ receptors) may be involved in certain pain states, and that positive allosteric modulators of these receptors may be useful analgesics (Mirza, N. R. and Munro, G., *Drug News and Perspectives*, 2010, 23(6), 351-360). 4-(Biphenyl-3-yl)-7H-imidazo[4,5-c]pyridazine derivatives have not been reported as having an interaction with $GABA_A$ $\alpha_{2/3}$ receptors. International patent applications PCT/GB01/04948 (published as WO2002/038568) and PCT/GB02/03114 (published as WO2003/008418) disclose 7-phenylimidazo[1,2-b][1,2,4]triazine derivatives that have affinity for the $\alpha_2$, $\alpha_3$ and/or $\alpha_5$ subunits. International patent application PCT/US99/14935 (published as WO2000/001697) discloses inter alia 4-phenyl-7H-imidazo[4,5-c]pyridazine derivatives which are corticotrophin releasing factor antagonists.

There is a continuing interest in finding new compounds that interact with $GABA_A$ receptors, and particularly for compounds that have a reduced propensity for causing the adverse events such as drowsiness that are associated with the currently available $GABA_A$ modulators such as benzodiazepines. It is thought that these adverse effects are a result of modulation of $\alpha_1$ subunit-containing receptors, and so preferred compounds will have a high affinity for the $\alpha_{2/3}$ subunit-containing receptors with good efficacy as positive allosteric modulators, while having low efficacy at receptors with other $\alpha$ subunits, particularly the $\alpha_1$ subunit-containing receptors.

These drug candidates should additionally have one or more of the following properties: be well absorbed from the gastrointestinal tract; be metabolically stable; have a good metabolic profile, in particular with respect to the toxicity or allergenicity of any metabolites formed; or possess favourable pharmacokinetic properties whilst still retaining their activity profile. They should be non-toxic and demonstrate few side-effects. Ideal drug candidates should exist in a physical form that is stable, non-hygroscopic and easily formulated.

SUMMARY OF THE INVENTION

In a first aspect, the present invention provides a compound of formula (I)

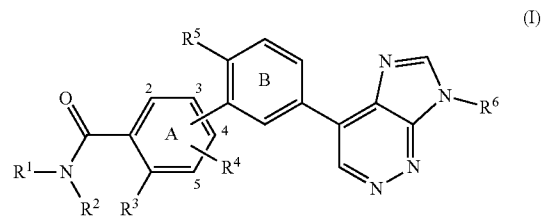

wherein:
  $R^1$ is selected from H and ($C_1$-$C_3$)alkyl:
  $R^2$ is selected from H and ($C_1$-$C_3$)alkyl and $R^3$ is H; or
  $R^2$ and $R^3$ together are —$CH_2$—;
  $R^4$ is selected from H, F and $OCH_3$;
  $R^5$ is selected from H and F; and
  $R^6$ is selected from ($C_2$-$C_4$)alkyl, ($C_3$-$C_5$)cycloalkyl and methyl-substituted ($C_3$-$C_5$)cycloalkyl,
and wherein
  ring B is attached to ring A at any one of positions 3, 4 and 5; and
  $R^4$ is attached to ring A at any one of positions 2, 3, 4 and 5,
  provided that $R^4$ and ring B cannot both be attached to ring A at the same position,
or a pharmaceutically acceptable salt thereof.

The compounds of formula (I) and their pharmaceutically acceptable salts are referred to herein as "the compounds of the invention". The definition above is referred to herein as embodiment E1 of this aspect. Further embodiments of this aspect of the invention are described in detail below.

In another aspect, the invention provides for a compound of formula (I) as described above, or in any one of the preferred embodiments, or a pharmaceutically acceptable salt thereof, for use as a medicament. In an embodiment according to this aspect the compound of formula (I), or a pharmaceutically acceptable salt thereof, is for use in the treatment of pain.

In another aspect, the invention provides for a pharmaceutical composition comprising a compound of formula (I) as described above, or in any one of the preferred embodiments, or a pharmaceutically acceptable salt thereof, and a pharmaceutically acceptable excipient.

In another aspect, the invention provides for a method of treating pain comprising administering a therapeutically effective amount of a compound of formula (I) as described above, or in any one of the preferred embodiments, or a pharmaceutically acceptable salt thereof, to an individual in need of such treatment.

In another aspect, the invention provides for the use of a compound of formula (I) as described above, or in any one of the preferred embodiments, or a pharmaceutically acceptable salt thereof, for the manufacture of a medicament for treating pain.

In another aspect, the invention provides for the use of a compound of formula (I) as described above, or in any one of the preferred embodiments, or a pharmaceutically acceptable salt thereof, for the treatment of pain.

In another aspect, the invention provides for a combination comprising a compound of formula (I) as described above, or in any one of the preferred embodiments, or a pharmaceutically acceptable salt thereof, and a second pharmaceutically active agent.

DETAILED DESCRIPTION OF THE INVENTION

Alkyl groups, containing the requisite number of carbon atoms, can be unbranched or branched. $(C_1-C_4)$Alkyl includes methyl, ethyl, n-propyl (1-propyl) and isopropyl (2-propyl, 1-methylethyl), n-butyl (1-butyl), sec-butyl (2-butyl, 1-methylpropyl), isobutyl (2-methylpropyl), and tert-butyl (1,1-dimethylethyl).

$(C_3-C_5)$Cycloalkyl includes cyclopropyl, cyclobutyl and cyclopentyl. Methyl-substituted $(C_3-C_5)$cycloalkyl includes 1-methylcyclopropyl, 2-methylcyclopropyl, 1-methylcyclobutyl, 2-methylcyclobutyl, 3-methylcyclobutyl, 1-methylcyclopentyl, 2-methylcyclopentyl and 3-methylcyclopentyl.

In compounds of formula (I) wherein $R^2$ and $R^3$ together are —$CH_2$—, it will be understood that the compound of formula (I) is a lactam of formula (II). The lactams of formula (II) represent a sub-genus within the compounds of formula (I).

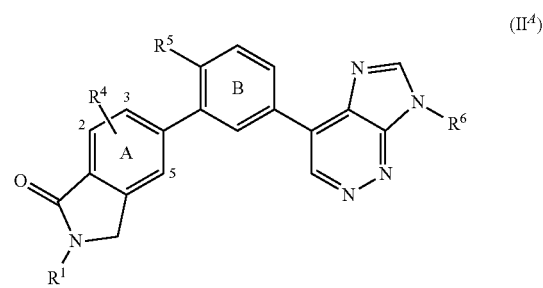

(II)

Further specific embodiments of the compounds of the invention are as follows.

In embodiment E2, there is provided a compound according to embodiment E1 in which ring B is attached to ring A at the 4-position according to formula ($I^4$)

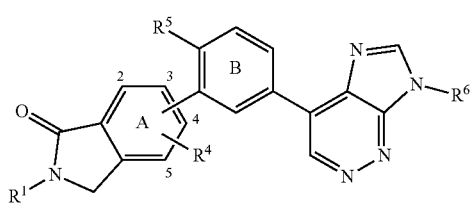

($I^4$)

wherein
$R^1$, $R^2$, $R^3$, $R^4$, $R^5$ and $R^6$ are as defined in embodiment E1, and wherein
$R^4$ is attached to ring A at any one of positions 2, 3 and 5,
or a pharmaceutically acceptable salt thereof.

In compounds of formula ($I^4$) wherein $R^2$ and $R^3$ together are —$CH_2$—, it will be understood that the compound of formula ($I^4$) is a lactam of formula ($II^4$). The lactams of formula ($II^4$) represent a sub-genus within the compounds of formula ($I^4$).

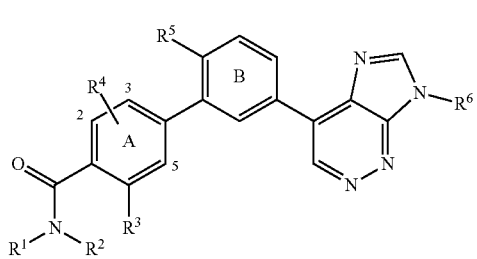

($II^4$)

In embodiment E3, there is provided a compound according to embodiment E1 in which ring B is attached to ring A at the 3-position according to formula ($I^B$)

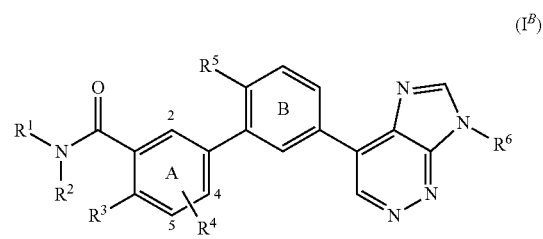

($I^B$)

wherein
$R^1$, $R^2$, $R^3$, $R^4$, $R^5$ and $R^6$ are as defined in embodiment E1,
and wherein
$R^4$ is attached to ring A at any one of positions 2, 4 and 5,
or a pharmaceutically acceptable salt thereof.

In compounds of formula ($I^B$) wherein $R^2$ and $R^3$ together are —$CH_2$—, it will be understood that the compound of formula ($I^B$) is a lactam of formula ($II^B$). The lactams of formula ($II^B$) represent a sub-genus within the compounds of formula ($I^B$).

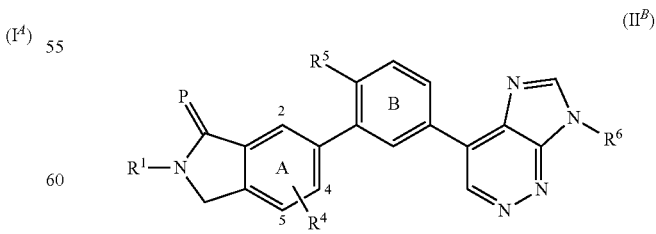

($II^B$)

In embodiment E4, there is provided a compound according to any one of embodiments E1, E2 or E3 or a pharmaceutically acceptable salt thereof, wherein $R^4$ is selected from H and $OCH_3$.

In embodiment E5, there is provided a compound according to any one of embodiments E1, E2, E3 or E4, or a pharmaceutically acceptable salt thereof, wherein $R^5$ is F.

Preferred compounds of the invention include:

5-[5-(7-ethyl-7H-imidazo[4,5-c]pyridazin-4-yl)-2-fluoro-phenyl]-6-methoxy-2-methyl-2,3-dihydro-isoindol-1-one, 5-[2-fluoro-5-(7-isopropyl-7H-imidazo[4,5-c]pyridazin-4-yl)-phenyl]-2-methyl-2, 3-dihydro-isoindol-1-one, 5-[5-(7-ethyl-7H-imidazo[4,5-c]pyridazin-4-yl)-2-fluoro-phenyl]-2-methyl-2,3-dihydro-isoindol-1-one, 5'-(7-ethyl-7H-imidazo[4,5-c]pyridazin-4-yl)-2'-fluoro-biphenyl-3-carboxamide, 6-[5-(7-ethyl-7H-imidazo[4,5-c]pyridazin-4-yl)-2-fluoro-phenyl]-2-methyl-2,3-dihydro-isoindol-1-one, and 5'-(7-ethyl-7H-imidazo[4,5-c]pyridazin-4-yl)-5,2'-difluoro-N-methyl-biphenyl-3-carboxamide, and pharmaceutically acceptable salts thereof.

Certain compounds of formula (I) include one or more stereogenic centers and so may exist as optical isomers, such as enantiomers and disastereomers. All such isomers and mixtures thereof are included within the scope of the present invention.

Hereinafter, all references to compounds of the invention include compounds of formula (I) or pharmaceutically acceptable salts, solvates, or multi-component complexes thereof, or pharmaceutically acceptable solvates or multi-component complexes of pharmaceutically acceptable salts of compounds of formula (I), as discussed in more detail below.

Preferred compounds of the invention are compounds of formula (I) or pharmaceutically acceptable salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/di hydrogen phosphate, pyroglutamate, saccharate, stearate, succinate, tannate, tartrate, tosylate, trifluoroacetate and xinofoate salts.

Hemisalts of acids and bases may also be formed, for example, hemisulphate salts.

The skilled person will appreciate that the aforementioned salts include ones wherein the counterion is optically active, for example d-lactate or l-lysine, or racemic, for example dl-tartrate or dl-arginine.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:

(i) by reacting the compound of formula (I) with the desired acid or base;
(ii) by removing an acid- or base-labile protecting group from a suitable precursor of the compound of formula (I) using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent.

The degree of ionisation in the resulting salt may vary from completely ionised to almost non-ionised.

The compounds of formula (I) or pharmaceutically acceptable salts thereof may exist in both unsolvated and solvated forms. The term 'solvate' is used herein to describe a molecular complex comprising a compound of formula (I) or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Also included within the scope of the invention are multi-component complexes (other than salts and solvates) of compounds of formula (I) or pharmaceutically acceptable salts thereof wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970), incorporated herein by reference.

The compounds of the invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of formula (I) with certain moieties known to those skilled in the art as 'pro-moieties' as described, for example, in "Design of Prodrugs" by H Bundgaard (Elsevier, 1985).

Examples of prodrugs include phosphate prodrugs, such as dihydrogen or dialkyl (e.g. di-tert-butyl) phosphate prodrugs. Further examples of replacement groups in accordance with the foregoing examples and examples of other prodrug types may be found in the aforementioned references.

Also included within the scope of the invention are metabolites of compounds of formula (I), that is, compounds formed in vivo upon administration of the drug. Some examples of metabolites in accordance with the invention include, where the compound of formula (I) contains a phenyl (Ph) moiety, a phenol derivative thereof (-Ph>-PhOH);

Compounds of the invention containing one or more asymmetric carbon atoms can exist as two or more stereoisomers. Included within the scope of the invention are all stereoisomers of the compounds of the invention and mixtures of one or more thereof.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Mixtures of stereoisomers may be separated by conventional techniques known to those skilled in the art; see, for example, "Stereochemistry of Organic Compounds" by E. L. Eliel and S. H. Wilen (Wiley, New York, 1994).

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I). It will be further appreciated that it may be necessary or desirable to carry out the transformations in a different order from that described in the schemes, or to modify one or more of the transformations, to provide the desired compound of the invention.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

All of the imidazopyridazine derivatives of the formula (I) can be prepared by the procedures described in the general methods presented below or by routine modifications thereof. The present invention also encompasses any one or more of these processes for preparing the imidazopyridazine derivatives of formula (I), in addition to any novel intermediates used therein.

According to a first process, compounds of formula (I) may be prepared from compounds of formula (IV) and (VI), as illustrated by Scheme 1.

Compounds of formulae (IV), (V) and (VI) are commercially available or may be synthesized by those skilled in the art according to the literature or preparations described herein.

Compounds of formula (I) may be prepared from compounds of formula (II) according to process step (iii), a Suzuki cross-coupling reaction with compounds of formula (V). Suzuki cross-coupling is conveniently effected in the presence of a suitable catalyst eg: palladium or nickel and a base. Typical conditions comprise a boronic acid or ester, a palladium catalyst with phosphine ligands in an organic solvent at elevated temperatures. Preferred Suzuki conditions comprise [1,1'-bis(diphenylphosphino)ferrocene]dichloro palladium(II), [1,1'-bis(di-tert-butylphosphino)ferrocene]dichloropalladium(II), tetrakis(triphenylphosphine)palladium(0), bis-(tri-tert-butylphosphine)palladium(0) or palladium acetate with cesium carbonate, sodium carbonate, potassium carbonate or diethylisopropylamine in dioxane, DMF or 2-methyl-2-butanol in water at elevated temperatures from 80-120° C. Wherein palladium acetate is used, a phosphine ligand is required such as 2-dicyclohexylphosphino-2,4,6-triisopropylbiphenyl.

Compounds of formula (II) may be prepared from compounds of formula (III) according to process step (ii), a cyclisation reaction with triethylorthoformate. Preferred conditions comprise heating compounds of formula (III) with triethylorthoformate at reflux. For compounds of formula (II) wherein X is iodo, halogen exchange may be effected from compounds of formula (II) wherein X is chloro according to reaction step (iia), a Finklestein reaction using sodium iodide in hydroiodic acid at 70° C.

Compounds of formula (III) may be prepared from compounds of formula (IV) according to process step (i), an aromatic nucleophilic substitution reaction. Typical conditions comprise heating neat with amines of formula (VI) at 120-150° C. for 12-48 hours.

According to a second process, compounds of formula (I) may be prepared from compounds of formula (VII) and (VIII), as illustrated by Scheme 2.

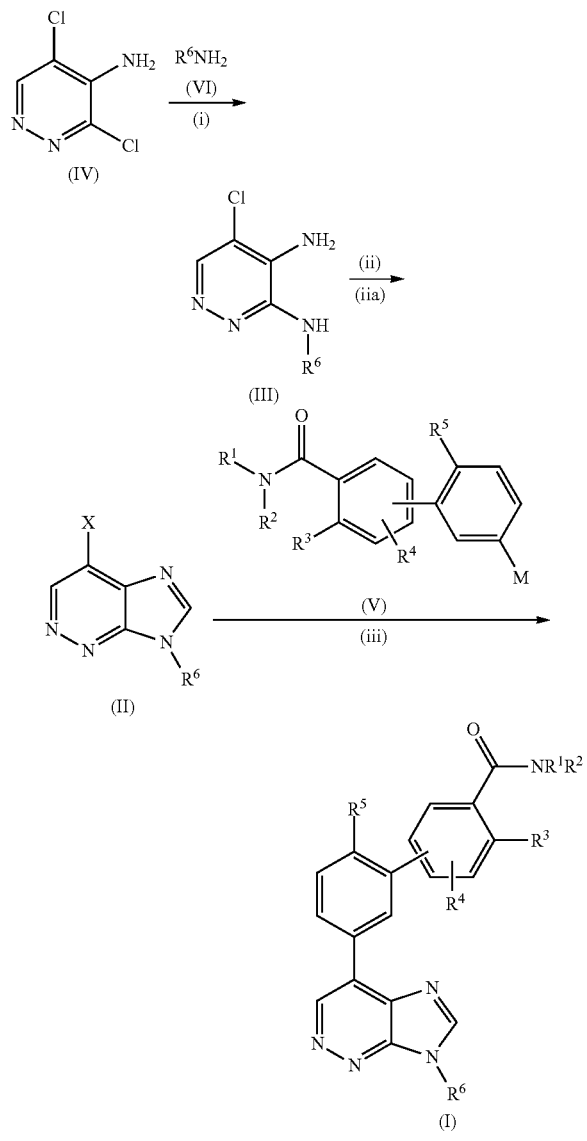

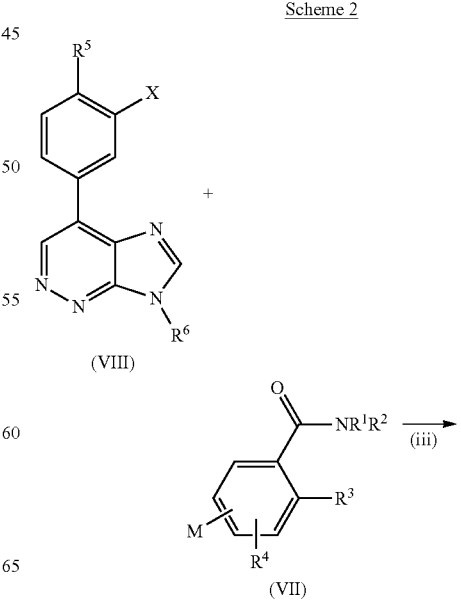

wherein X is Cl, Br, I; and M is boronic acid or ester

-continued

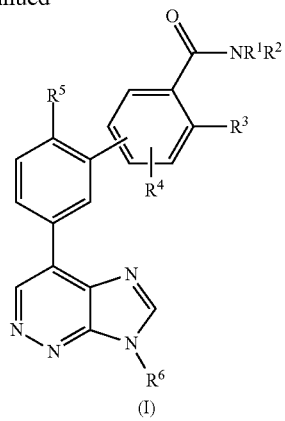

(I)

wherein X is Cl, Br, I; and M is boronic acid or ester.

Compounds of formula (VII) are commercially available or may be synthesized by those skilled in the art according to the method set out in Scheme 6, or to the literature or preparations described herein.

Compounds of formula (VIII) are described in Scheme 5.

Compounds of formula (I) may be prepared from compounds of formula (VIII) according to process step (iii), a Suzuki cross-coupling reaction with compounds of formula (VII) as described in Scheme 1.

According to a third process, compounds of formula (I) may be prepared from compounds of formula (X) and (IX), as illustrated by Scheme 3.

Scheme 3

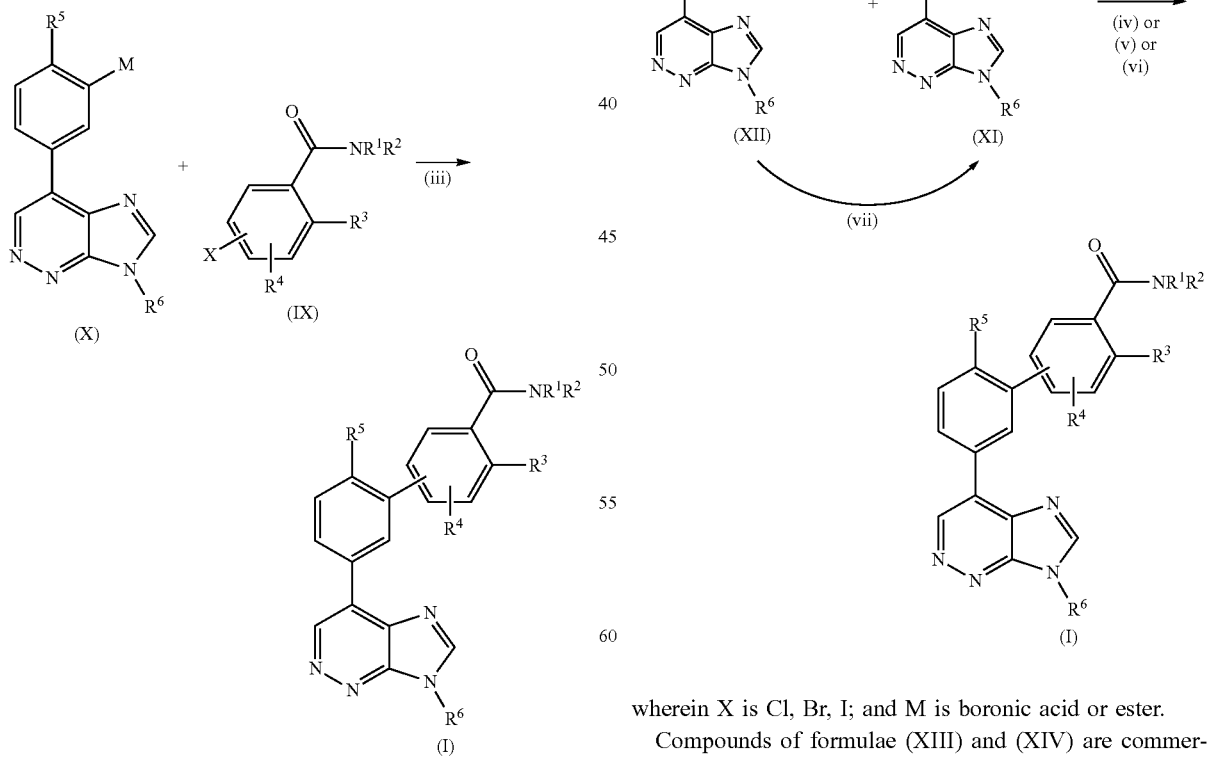

wherein X is Cl, Br, I; and M is boronic acid or ester.

Compounds of formula (IX) are commercially available or may be synthesized by those skilled in the art according to the method set out in Scheme 7, or to the literature or preparations described herein.

Compounds of formula (X) are described in Scheme 5.

Compounds of formula (I) may be prepared from compounds of formula (X) according to process step (iii), a Suzuki cross-coupling reaction with compounds of formula (IX) as described in Scheme 1.

According to a fourth process, compounds of formula (I) may be prepared from compounds of formula (X) and (XIII), as illustrated by Scheme 4.

Scheme 4

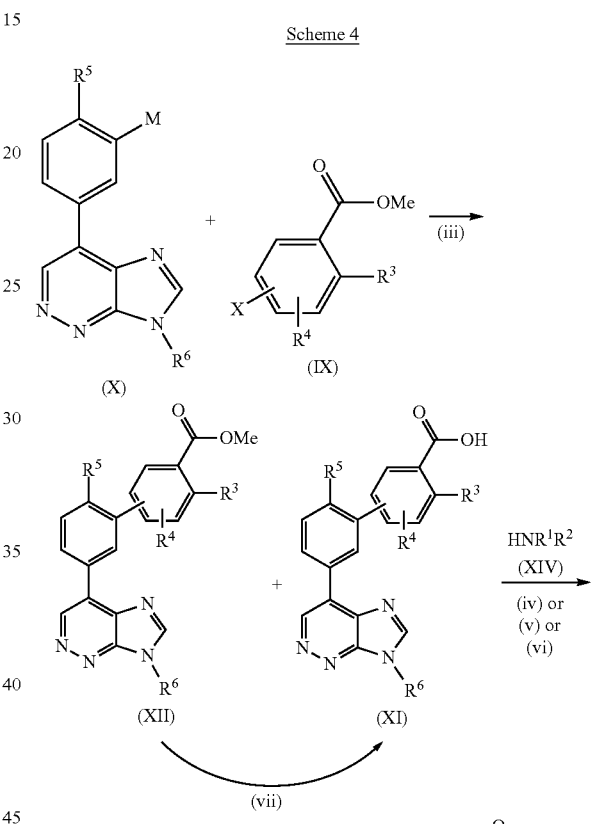

wherein X is Cl, Br, I; and M is boronic acid or ester.

Compounds of formulae (XIII) and (XIV) are commercially available or may be synthesized by those skilled in the art according to the literature or preparations described herein.

Compounds of formula (X) are described in Scheme 5.

Compounds of formula (I) may be prepared from compounds of formula (XII) according to process step (iv), an amide bond formation step through direct displacement of an ester. Preferred conditions comprise heating compounds of formula (XII) with amines of formula (XIV) in methanol at elevated temperatures in a Reactivial™.

Compounds of formula (I) may also be prepared from compounds of formula (XI) according to process step (v), an amide bond formation using a suitable base such as DIPEA, a suitable coupling agent such as HATU, HBTU or EDCI with HOBt and a suitable amine of general formula (XIV). Preferred conditions comprise EDCI with HOBt and NMM in dioxane at room temperature. Alternatively compounds of formula (I) may be prepared from compounds of formula (XI) according to process step (vi), an amide bond formation step via an acid chloride intermediate. Typical conditions comprise oxalyl chloride in DCM with catalytic DMF followed by amines of general formula (XIV) in DCM at room temperature.

Compounds of formula (XI) may be prepared from compounds of formula (XII) according to process step (vii) a hydrolysis reaction using a suitable base such as sodium or lithium hydroxide in a suitable solvent combination such as THF or dioxane in water. Preferred conditions comprise LiOH in THF and water at room temperature. Compounds of formula (XI) may also be prepared from compounds of formulae (X) and (XIII) according to process step (iii) as described in Scheme 1 where hydrolysis occurs during the Suzuki reaction.

Compounds of formula (XII) may be prepared from compounds of formulae (X) and (XIII) according to process step (iii) as described in Scheme 1.

According to a fifth process, compounds of formulae (VIII) and (X) may be prepared from compounds of formula (II), (XVI) or (XVII) as illustrated by Scheme 5.

wherein X is Cl, Br, I; and M is boronic acid, ester or diazaborine.

Compounds of formulae (XVI) and (XVII) are commercially available or may be synthesized by those skilled in the art according to the literature or preparations described herein.

Compounds of formula (II) are described in Scheme 1.

Compounds of formula (VIII) may be prepared from compounds of formula (XV) according to process step (viii), an electrophilic halogenation reaction. Typical conditions comprise 1,3-dibromo-5,5-dimethylhydantoin or 1,3-di-iodo-5,5-dimethylhydantoin in concentrated sulfuric acid at 0° C.

Compounds of formula (X) may be prepared from compounds of formula (VIII) according to process step (ix) a palladium catalysed borylation reaction. Typical conditions comprise bispinacolatodiboron and potassium acetate in dioxane with 1,1'-bis(diphenylphosphino)ferrocene palladium (II) dichloride at 100° C.

Compounds of formulae (VIII) or (X) may also be prepared from compounds of formula (II) according to process step (iii) with compounds of formula (XVII) as described in Scheme 1.

Compounds of formula (XV) may be prepared from compounds of formula (II) according to process step (iii) with compounds of formula (XVI) as described in Scheme 1.

When M is diazaborine, the boronic acid may be unmasked by using a suitable inorganic acid in the presence of a suitable organic solvent. Preferred conditions comprise 5N aqueous HCl in THF at reflux for 16 hours.

According to a sixth process, compounds of formula (VII$^4$) (i.e. compounds of formula (VII) wherein $R^2$ and $R^3$ together are —CH$_2$—) may be prepared from compounds of formula (XX) as illustrated by Scheme 6.

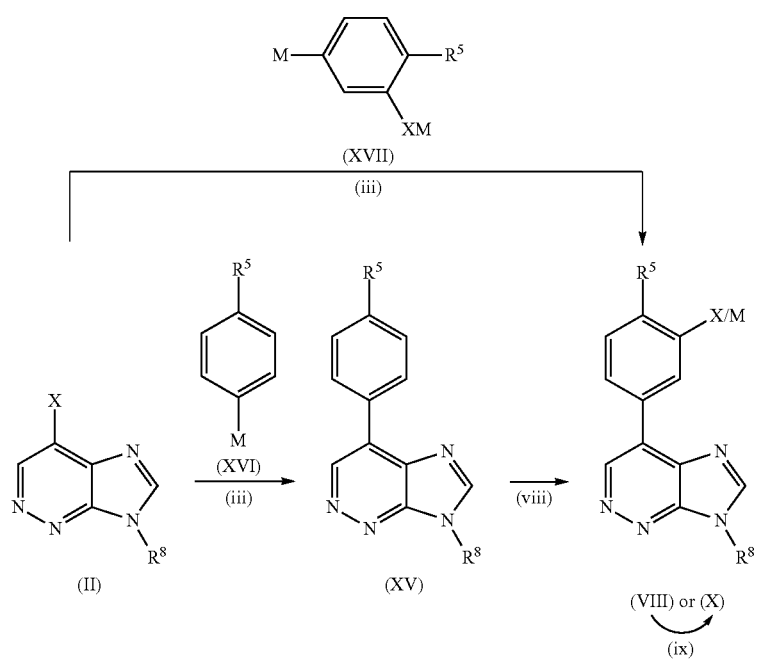

Scheme 6

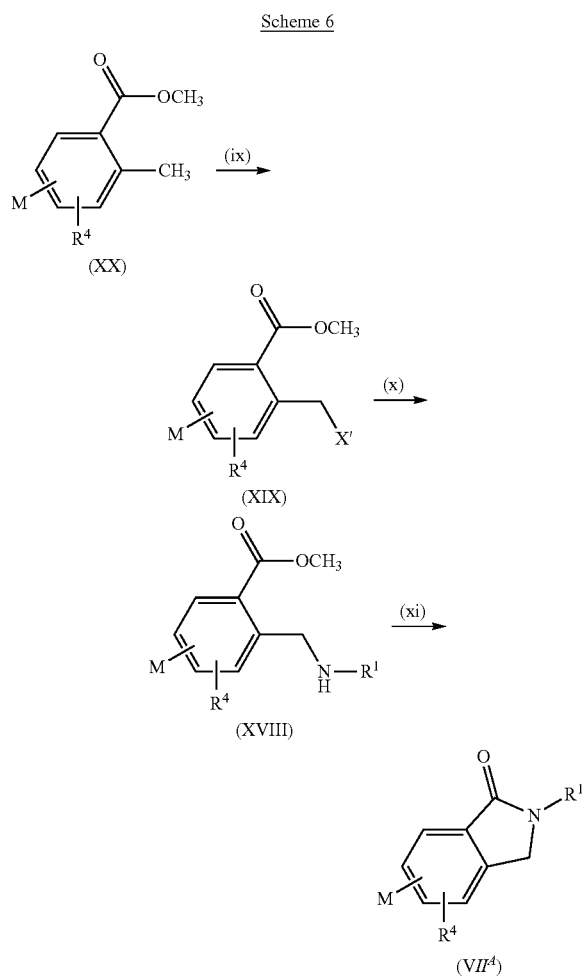

Scheme 7

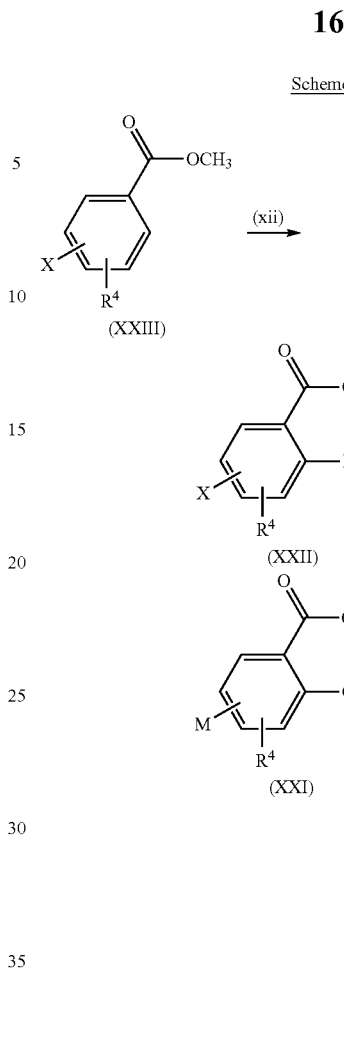

wherein M is boronic acid or ester, and X' is Cl, Br or I

Compounds of formula (VII$^4$) may be prepared from compounds of formula (XVIII) according to the process step (xi), which is a thermal cyclization reaction. The compound of formula (XVIII) is heated in a suitable solvent, such as methanol or acetonitrile, preferably at reflux.

Compounds of formula (XVIII) may be prepared from compounds of formula (XIX) according to the process step (x), which is an amine alkylation reaction. The compound of formula (XIX) is treated with ammonia (R$^1$=H) or a primary amine (R$^1$=alkyl) in a suitable solvent such as methanol.

Compounds of formula (XIX) may be prepared from compounds of formula (XX) according to the process step (ix), which is a free-radical halogenation reaction. Preferred conditions comprise treating the compound of formula (XX) with N-bromosuccinimide and a radical initiator such as benzoyl peroxide in a suitable solvent such as carbon tetrachloride.

According to a seventh process, compounds of formula (IX$^4$) (i.e. compounds of formula (IX) wherein R$^1$ is H and R$^2$ and R$^3$ together are —CH$_2$—) may be prepared from compounds of formula (XXIII) as illustrated by Scheme 7.

Compounds of formula (IX$^4$) may be prepared from compounds of formula (XXI) according to the process step (xiv), which is a reduction/cyclization reaction. The compound of formula (XXI) is hydrogenated in the presence of a Raney Nickel catalyst and aqueous ammonia in a suitable solvent, such as methanol. The primary amine so produced cyclizes spontaneously to give the lactam of formula (IX$^4$).

Compounds of formula (XXI) may be prepared from compounds of formula (XXII) according to the process step (xiii), which is a cyanation reaction. The compound of formula (XXII) is treated with copper(I) cyanide in a suitable solvent such as dimethylformamide at an elevated temperature.

Compounds of formula (XXII) may be prepared from compounds of formula (XXIII) according to the process step (xii), which is an electrophilic halogenation reaction. The compound of formula (XX) is treated with bromine in a suitable solvent such as a mixture of acetic acid in water.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In another aspect the invention provides a pharmaceutical composition comprising a compound of the invention together with one or more pharmaceutically acceptable excipients.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Suitable modes of administration include oral, parenteral, topical, inhaled/intranasal, rectal/intravaginal, and ocular/aural administration.

Formulations suitable for the aforementioned modes of administration may be formulated to be immediate and/or modified release. Modified release formulations include delayed-, sustained-, pulsed-, controlled-, targeted and programmed release.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

In the case of dry powder inhalers and aerosols, the dosage unit is determined by means of a valve which delivers a metered amount. Units in accordance with the invention are typically arranged to administer a metered dose or "puff" containing from 1 µg to 100 mg of the compound of formula (I). The overall daily dose will typically be in the range 1 µg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 0.1 mg to 10 g, such as 1 mg to 1 g, for example 2.5 mg to 500 mg depending, of course, on the mode of administration and efficacy. For example, oral administration may require a total daily dose of from 5 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

The compounds of the invention are useful because they exhibit pharmacological activity, i.e., $GABA_A$ channel modulation. More particularly, the compounds of the invention are positive allosteric modulators of the $GABA_A$ channel. Preferred compounds of the invention are selective modulators of the $\alpha_2$, $\alpha_3$ and/or $\alpha_5$ subtypes, with lower efficacy and/or affinity at the $\alpha_1$, $\alpha_4$ and/or $\alpha_6$ subtypes. The compounds of the invention are accordingly of use in the treatment of disorders in animals for which a $GABA_A$ positive allosteric modulator is indicated. Preferably the animal is a mammal, more preferably a human.

In a further aspect of the invention there is provided a compound of the invention for use as a medicament.

In a further aspect of the invention there is provided a compound of the invention for the treatment of a disorder for which a $GABA_A$ positive allosteric modulator is indicated.

In a further aspect of the invention there is provided use of a compound of the invention for the preparation of a medicament for the treatment of a disorder for which a $GABA_A$ positive allosteric modulator is indicated.

In a further aspect of the invention there is provided a method of treating a disorder in an animal (preferably a mammal, more preferably a human) for which a $GABA_A$ positive allosteric modulator is indicated, comprising administering to said animal a therapeutically effective amount of a compound of the invention.

The $GABA_A$ positive allosteric modulators of formula (I) may be used:
- as analgesics, for example for the treatment of pain, including acute pain, chronic pain, neuropathic pain, nociceptive (including inflammatory) pain, somatic pain, visceral pain, and dysfunctional pain, as further discussed below, and in particular for pain conditions wherein there is a brain or spinal component to the underlying mechanism;
- as anticonvulsants, for example for the treatment of epilepsy and epilepsy associated disorders, including Lennox-Gastaut syndrome, Dravet's disease, and generalised epilepsy with febrile seizures plus (GEFS+);
- as anxiolytic agents, for example for the treatment of panic disorder, generalized anxiety disorder, stress disorders such as post-traumatic stress disorder, acute stress disorder and substance-induced stress disorder, phobias such as agoraphobia, social phobia and animal phobias, and obsessive-compulsive disorder; and
- as muscle relaxants, for example for the treatment of muscle spasm, dystonia, spasticity (including generalised and focal spasticity) and essential tremor.

The $GABA_A$ positive allosteric modulators of formula (I) may also be used for the treatment of autism, or as antipsychotic agents, for example for the treatment of schizophrenia.

Other therapeutic indications for the $GABA_A$ positive allosteric modulators of formula (I) include use as antidepressant agents, for example for the treatment of depressive and bipolar disorders and cyclothymia; as antiemetic agents, for example for the treatment of chemotherapy- or radiation-induced emesis, post-operative nausea and vomiting, and motion sickness; as cognition-enhancing agents, for example for the treatment of neurodegenerative disorders, such as Alzheimer's disease, and cerebral ischemia; as sleep improving agents, for example for the treatment of sleep disorders such as insomnia and circadian rhythm disorders such as jet-lag, or for use as pre-medication prior to anaesthesia or endoscopy; and use in the treatment of addiction phenotypes such as alcoholism, Angelman syndrome, attention deficit hyperactivity disorder, bladder urgency, bowel abnormalities, eating disorders such as anorexia nervosa and bulimia nervosa, Fragile X syndrome, hearing disorders such as tinnitus and age-related hearing impairment, multiple sclerosis, neuroses, overactive bladder with sensory disturbance, premenstrual syndrome, restless legs syndrome, and urinary incontinence.

A preferred use for the compounds of formula (I) is the treatment of pain. Pain may be either acute or chronic and additionally may be of central and/or peripheral origin. Pain may be of a neuropathic and/or nociceptive and/or inflammatory nature, such as pain affecting either the somatic or visceral systems, as well as dysfunctional pain affecting multiple systems.

Physiological pain is an important protective mechanism designed to warn of danger from potentially injurious stimuli from the external environment. The system operates through a specific set of primary sensory neurones and is activated by noxious stimuli via peripheral transducing mechanisms (see Meyer et al., 2006, Wall and Melzack's Textbook of Pain ($5^{th}$ Ed), Chapter 1). These sensory fibres are known as nociceptors, and are characteristically small diameter axons with slow conduction velocities, of which there are two main types, A-delta fibres (myelinated) and C fibres (non-myelinated). Nociceptors encode the intensity, duration and quality of noxious stimulus and by virtue of their topographically organised projection to the spinal cord, the location of the stimulus. The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually, although not always, associated with a specific cause such as a defined injury, is often sharp and severe and can result from numerous origins such as surgery, dental work, a strain or a sprain. Acute pain does not generally result in any persistent psychological response. When a substantial injury occurs to body tissue, via disease or trauma, the characteristics of nociceptor activation may be altered such that there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury or alteration which can be associated with maladaptation and aberrant activity (Woolf & Salter, 2000, Science, 288, 1765-1768). As such, chronic pain is long-term pain, typically persisting for more than three months and leading to significant psychological and emotional problems. Common examples of chronic pain are neuropathic pain (e.g. painful diabetic neuropathy or postherpetic neuralgia), carpal tunnel syndrome, back pain, headache, cancer pain, arthritic pain and chronic post-surgical pain, but may include any chronic painful condition affecting any system, such as those described by the International Association for the Study of Pain (Classification of Chronic Pain, a publication freely available for download at http://www.iasp-pain.org).

The clinical manifestation of pain is present when discomfort and abnormal sensitivity feature among the patient's symptoms. Patients tend to be quite heterogeneous and may present with various pain symptoms. Such symptoms can include: 1) spontaneous pain which may be dull, burning, or stabbing; 2) exaggerated pain responses to noxious stimuli (hyperalgesia); and 3) pain produced by normally innocuous stimuli (allodynia) (Meyer et al., 2006, Wall and Melzack's Textbook of Pain (5$^{th}$ Ed), Chapter 1). Although patients suffering from various forms of acute and chronic pain may have similar symptoms, the underlying mechanisms may be different and may, therefore, require different treatment strategies. Apart from acute or chronic, pain can also be broadly categorized into: nociceptive pain, affecting either the somatic or visceral systems, which can be inflammatory in nature (associated with tissue damage and the infiltration of immune cells); or neuropathic pain.

Nociceptive pain can be defined as the process by which intense thermal, mechanical, or chemical stimuli are detected by a subpopulation of peripheral nerve fibers, called nociceptors, and can be induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 2006, Wall and Melzack's Textbook of Pain (5$^{th}$ Ed), Chapter 1). Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from strains/sprains, burns, myocardial infarction and acute pancreatitis, post-operative pain (pain following any type of surgical procedure), posttraumatic pain, pain associated with gout, cancer pain and back pain. Cancer pain may be chronic pain such as tumour related pain (e.g. bone pain, headache, facial pain or visceral pain) or pain associated with cancer therapy (e.g. in response to chemotherapy, immunotherapy, hormonal therapy or radiotherapy). Back pain may be due to herniated or ruptured intervertabral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Nociceptive pain can also be related to inflammatory states. The inflammatory process is a complex series of biochemical and cellular events, activated in response to tissue injury or the presence of foreign substances, which results in swelling and pain (McMahon et al., 2006, Wall and Melzack's Textbook of Pain (5$^{th}$ Ed), Chapter 3). A common inflammatory condition associated with pain is arthritis. It has been estimated that almost 27 million Americans have symptomatic osteoarthritis (OA) or degenerative joint disease (Lawrence et al., 2008, Arthritis Rheum, 58, 15-35); most patients with osteoarthritis seek medical attention because of the associated pain. Arthritis has a significant impact on psychosocial and physical function and is known to be the leading cause of disability in later life. Rheumatoid arthritis is an immune-mediated, chronic, inflammatory polyarthritis disease, mainly affecting peripheral synovial joints. It is one of the commonest chronic inflammatory conditions in developed countries and is a major cause of pain.

In regard to nociceptive pain of visceral origin, visceral pain results from the activation of nociceptors of the thoracic, pelvic, or abdominal organs (Bielefeldt and Gebhart, 2006, Wall and Melzack's Textbook of Pain (5$^{th}$ Ed), Chapter 48). This includes the reproductive organs, spleen, liver, gastrointestinal and urinary tracts, airway structures, cardiovascular system and other organs contained within the abdominal cavity. As such visceral pain refers to pain associated with conditions of such organs, such as painful bladder syndrome, interstitial cystitis, prostatitis, ulcerative colitis, Crohn's disease, renal colic, irritable bowl syndrome, endometriosis and dysmenorrheal (Classification of Chronic Pain, available at http://www.iasp-pain.org). Currently the potential for a neuropathic contribution (either through central changes or nerve injury/damage) to visceral pain states is poorly understood but may play a role in certain conditions (Aziz et al., 2009, Dig Dis 27, Suppl 1, 31-41)

Neuropathic pain is currently defined as pain arising as a direct consequence of a lesion or disease affecting the somatosensory system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Dworkin, 2009, Am J Med, 122, S1-S2; Geber et al., 2009, Am J Med, 122, S3-S12; Haanpaa et al., 2009, Am J Med, 122, S13-S21). The symptoms of neuropathic pain are difficult to treat, as they are often heterogeneous even between patients with the same disease (Dworkin, 2009, Am J Med, 122, S1-S2; Geber et al., 2009, Am J Med, 122, S3-S12; Haanpaa et al., 2009, Am J Med, 122, S13-S21). They include spontaneous pain, which can be continuous, and paroxysmal or abnormal evoked pain, such as hyperalgesia (increased sensitivity to a noxious stimulus) and allodynia (sensitivity to a normally innocuous stimulus).

It should be noted that some types of pain have multiple aetiologies and thus can be classified in more than one area, e.g. back pain, cancer pain and even migraine headaches may include both nociceptive and neuropathic components.

Similarly other types of chronic pain, perhaps less well understood, are not easily defined by the simplistic definitions of nociceptive or neuropathic. Such conditions include in particular fibromyalgia and chronic regional pain syndrome, which are often described as dysfunctional pain states e.g. fibromyalgia or complex regional pain syndrome (Woolf, 2010, J Clin Invest, 120, 3742-3744), but which are included in classifications of chronic pain states (Classification of Chronic Pain, available at http://www.iasp-pain.org).

A $GABA_A$ positive allosteric modulator may be usefully combined with another pharmacologically active compound, or with two or more other pharmacologically active compounds, particularly in the treatment of pain. Such combinations offer the possibility of significant advantages, including patient compliance, ease of dosing and synergistic activity.

In the combinations that follow the compound of the invention may be administered simultaneously, sequentially or separately in combination with the other therapeutic agent or agents.

For the treatment of pain, a $GABA_A$ positive allosteric modulator of formula (I), or a pharmaceutically acceptable salt thereof, as defined above, may be administered in combination with one or more agents selected from:

a selective Nav1.3 channel modulator, such as a compound disclosed in WO2008/118758;

a selective Nav1.7 channel modulator, such as a compound disclosed in WO2010/079443, e.g. 4-[2-(5-amino-1H-pyrazol-4-yl)-4-chlorophenoxy]-5-chloro-2-fluoro-N-1,3-thiazol-4-ylbenzenesulfonamide or 4-[2-(3-amino-1H-pyrazol-4-yl)-4-(trifluoromethyl)phenoxy]-5-chloro-2-fluoro-N-1,3-thiazol-4-ylbenzenesulfonamide, or a pharmaceutically acceptable salt of either;

a selective Nav1.8 channel modulator;

a selective Nav1.9 channel modulator;

a compound which modulates activity at more than one Nav channel, including a non-selective modulator such as bupivacaine, carbamazepine, lamotrigine, lidocaine, mexiletine or phenytoin;

any inhibitor of nerve growth factor (NGF) signaling, such as: an agent that binds to NGF and inhibits NGF biological activity and/or downstream pathway(s) mediated by NGF signaling (e.g. tanezumab), a TrkA antagonist or a p75 antagoinsist, or an agent that inhibits downstream signaling in regard to NGF stimulated TrkA or P75 signalling;

an inhibitor of neurotrophic pathways, where such inhibition is achieved by: (a) an agent that binds to nerve growth factor (NGF) (e.g. tanezumab, fasinumab or fulranumab), brain-derived neurotrophic factor (BDNF), neurotrophin-3 (NT-3) or neurotrophin-4 (NT-4), or to more than one of the aforementioned neurotrophins (e.g. soluble P75); or (b) an agent that inhibits receptor function at one or more of TrKA, TrKB, TrKC or P75, either at the orthosteric site, an allosteric site or by inhibition of the catalytic activity of the receptor(s);

a compound which increases the levels of endocannabinoid, such as a compound with fatty acid amid hydrolase inhibitory (FAAH) or monoacylglycerol lipase (MAGL) activity;

an analgesic, in particular paracetamol;

an opioid analgesic, such as: buprenorphine, butorphanol, cocaine, codeine, dihydrocodeine, fentanyl, heroin, hydrocodone, hydromorphone, levallorphan levorphanol, meperidine, methadone, morphine, nalmefene, nalorphine, naloxone, naltrexone, nalbuphine, oxycodone, oxymorphone, propoxyphene or pentazocine;

an opioid analgesic which preferentially stimulates a specific intracellular pathway, for example G-protein as opposed to beta arrestin recruitment, such as TRV130; an opioid analgesic with additional pharmacology, such as: noradrenaline (norepinephrine) reuptake inhibitory (NRI) activity, e.g. tapentadol; serotonin and norepinephrine reuptake inhibitory (SNRI) activity, e.g. tramadol; or nociceptin receptor (NOP) agonist activity, such as GRT6005;

a nonsteroidal antiinflammatory drug (NSAID), such as a non-selective cyclooxygenase (COX) inhibitor, e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac; or a COX-2 selective inhibitor, e.g. celecoxib, deracoxib, etoricoxib, mavacoxib or parecoxib;

a prostaglandin $E_2$ subtype 4 (EP4) antagonist;

a microsomal prostaglandin E synthase type 1 (mPGES-1) inhibitor;

a sedative, such as glutethimide, meprobamate, methaqualone or dichloralphenazone;

a $GABA_A$ modulator with broad subtype modulatory effects mediated via the benzodiazepine binding site, such as chlordiazepoxide, alprazolam, diazepam, lorazepam, oxazepam, temazepam, triazolam, clonazepam or clobazam;

a $GABA_A$ modulator with subtype-selective modulatory effects mediated via the benzodiazepine binding site with reduced adverse effects, for example sedation, such as TPA023, TPA023B, L-838,417, CTP354 or NSD72;

a $GABA_A$ modulator acting via alternative binding sites on the receptor, such as barbiturates, e.g. amobarbital, aprobarbital, butabital, mephobarbital, methohexital, pentobarbital, phenobartital, secobarbital, or thiopental; neurosteroids such as alphaxalone, alphadolone or ganaxolone; β-subunit ligands, such as etifoxine; or δ-preferring ligands, such as gaboxadol;

a GlyR3 agonist or positive allosteric modulator;

a skeletal muscle relaxant, e.g. baclofen, carisoprodol, chlorzoxazone, cyclobenzaprine, metaxolone, methocarbamol or orphrenadine;

a glutamate receptor antagonist or negative allosteric modulator, such as an NMDA receptor antagonist, e.g. dextromethorphan, dextrorphan, ketamine or, memantine; or an mGluR antagonist or modulator;

an alpha-adrenergic, such as clonidine, guanfacine or dexmetatomidine;

a beta-adrenergic such as propranolol;

a tricyclic antidepressant, e.g. desipramine, imipramine, amitriptyline or nortriptyline;

a tachykinin (NK) antagonist, such as aprepitant or maropitant;

a muscarinic antagonist, e.g oxybutynin, tolterodine, propiverine, tropsium chloride, darifenacin, solifenacin, temiverine and ipratropium;

a cholinergic (nicotinic) analgesic, such as ispronicline (TC-1734), varenicline or nicotine;

a Transient Receptor Potential V1 (TRPV1) receptor agonist (e.g. resinferatoxin or capsaicin) or antagonist (e.g. capsazepine or mavatrap);

a Transient Receptor Potential A1 (TRPA1) receptor agonist (e.g. cinnamaldehyde or mustard oil) or antagonist (e.g. GRC17536 or CB-625);

a Transient Receptor Potential M8 (TRPM8) receptor agonist (e.g. menthol or icilin) or antagonist;

a Transient Receptor Potential V3 (TRPV3) receptor agonist or antagonist (e.g. GRC-15300);

a corticosteroid such as dexamethasone;

a 5-HT receptor agonist or antagonist, particularly a $5-HT_{1B/1D}$ agonist, such as eletriptan, sumatriptan, naratriptan, zolmitriptan or rizatriptan;

a $5-HT_{2A}$ receptor antagonist;

a PDEV inhibitor, such sildenafil, tadalafil or vardenafil;

an alpha-2-delta ligand such as gabapentin, gabapentin enacarbil or pregabalin;

a serotonin reuptake inhibitor (SRI) such as sertraline, demethylsertraline, fluoxetine, norfluoxetine, fluvoxamine, paroxetine, citalopram, desmethylcitalopram, escitalopram, d,l-fenfluramine, femoxetine, ifoxetine, cyanodothiepin, litoxetine, dapoxetine, nefazodone, cericlamine and trazodone;

an NRI, such as maprotiline, lofepramine, mirtazepine, oxaprotiline, fezolamine, tomoxetine, mianserin, buproprion, buproprion metabolite hydroxybuproprion, nomifensine and viloxazine, especially a selective noradrenaline reuptake inhibitor such as reboxetine;

an SNRI, such as venlafaxine, O-desmethylvenlafaxine, clomipramine, desmethylclomipramine, duloxetine, milnacipran and imipramine;

an inducible nitric oxide synthase (iNOS) inhibitor;

a leukotriene B4 antagonist;

a 5-lipoxygenase inhibitor, such as zileuton;

a potassium channel opener or positive modulator, such as an opener or positive modulator of KCNQ/Kv7 (e.g. retigabine or flupirtine), a G protein-coupled inwardly-rectifying potassium channel (GIRK), a calcium-activated potassium channel (Kca) or a potassium voltage-gated channel such as a member of subfamily A (e.g. Kv1.1), subfamily B (e.g. Kv2.2) or subfamily K (e.g. TASK, TREK or TRESK);

a $P2X_3$ receptor antagonist (e.g. AF219) or an antagonist of a receptor which contains as one of its subunits the $P2X_3$ subunit, such as a $P2X_{2/3}$ heteromeric receptor;

a $Ca_v2.2$ calcium channel blocker (N-type), such as ziconotide; and a $Ca_v3.2$ calcium channel blocker (T-type), such as ethosuximide.

There is also included within the scope the present invention combinations of a compound of the invention together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include ritonavir, saquinavir, ketoconazole, N-(3,4-difluorobenzyl)-N-methyl-2-{[(4-methoxypyridin-3-yl)amino]sulfonyl}benzamide and N-(1-(2-(5-(4-fluorobenzyl)-3-(pyridin-4-yl)-1H-pyrazol-1-yl)acetyl)piperidin-4-yl) methanesulfonamide.

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which a $Na_v1.8$ modulator is indicated.

It is to be appreciated that all references herein to treatment include curative, palliative and prophylactic treatment.

In the non-limiting Examples and Preparations that are set out later in the description, and in the aforementioned Schemes, the following the abbreviations, definitions and analytical procedures may be referred to:

AcOH is acetic acid;
aq is aqueous;
br is broad;
° C. is degrees Celcius
$CDCl_3$ is deutero-chloroform;
$Cs_2CO_3$ is cesium carbonate;
δ is chemical shift;
d is doublet;
DCM is dichloromethane; methylene chloride;
DIPEA is N-ethyldiisopropylamine, N,N-diisopropylethylamine;
DMF is N,N-dimethylformamide;
DMSO is dimethyl sulphoxide;
EDCI.HCl is 1-(3-dimethylaminopropyl)-3-ethylcarbodiimide hydrochloride;
ELSD is evaporative light scattering detection;
EtOAc is ethyl acetate;
EtOH is ethanol;
g is gram;
HCl is hydrochloric acid;
HOBt is N-hydroxybenzotriazole hydrate;
HPLC is high pressure liquid chromatography;
L is liter;
LCMS is liquid chromatography mass spectrometry (Rt=retention time);
m is multiplet;
M is molar;
MeCN is acetonitrile;
MeOH is methanol;
mg is milligram;
$MgSO_4$ is magnesium sulphate;
MHz is megaHertz;
min is minutes;
mL is milli liter;
mmol is millimole;
mol is mole;
MS m/z is mass spectrum peak;
NaH is sodium hydride;
$NaHCO_3$ is sodium hydrogencarbonate;
$Na_2CO_3$ is sodium carbonate;
NaOH is sodium hydroxide;
$Na_2SO_4$ is sodium sulphate;
NBS is N-bromosuccinimide
$NH_4OH$ is ammonium hydroxide;
NMM is N-methylmorpholine;
NMR is nuclear magnetic resonance;
ODS is octadecylsilyl;
pH is power of hydrogen;
$POCl_3$ is phosphorusoxychloride;
ppm is parts per million;
q is quartet;
Rt is retention time;
s is singlet;
SCX is strong cation exchange;
t is triplet;
TBME is tert-butyl dimethyl ether;
TFA is trifluoroacetic acid;
THF is tetrahydrofuran;
TLC is thin layer chromatography;
μL is microliter; and
μmol is micromol The Preparations and Examples that follow illustrate the invention but do not limit the invention in any way. All starting materials are available commercially or described in the literature. All temperatures are in ° C. Silica gel column chromatography was carried out using Merck silica gel 60 (9385). Thin layer chromatography (TLC) was carried out on Merck silica gel 60 plates (5729). $^1$H- and $^{19}$F-NMR spectra were recorded on a Varian Mercury 300 or 400 MHz, Bruker Avance 400 MHz NMR or Jeol ECX 400 MHz. When peak multiplicities are reported, the following abbreviations are used: s=singlet, d=doublet, t=triplet, m=multiplet, br=broadened, dd=doublet of doublets, dt=doublet of triplets.

LCMS indicates liquid chromatography mass spectrometry ($R_t$=retention time). Where ratios of solvents are given, the ratios are by volume.

Mass spectra (MS) were recorded using either electrospray ionisation (ESI) or atmospheric pressure chemical ionisation (APCI). Mass spectroscopy was carried out using a Finnigan Navigator single quadrupole electrospray mass spectrometer, Finnigan aQa APCI mass spectrometer or Applied Biosystem Q-Trap Where it is stated that compounds were prepared in the manner described for an earlier Preparation or Example, the skilled person will appreciate that reaction times, number of equivalents of reagents and reaction temperatures may have been modified for each specific reaction, and that it may nevertheless be necessary, or desirable, to employ different work-up or purification conditions.

Preparative HPLC:

Where singleton compounds are purified by preparative HPLC, there are two methods used, shown below:
Method 1 Acidic Conditions
Column Gemini NX C18, 5 um 21.2×100 mm
Temperature Ambient
Detection ELSD-MS
Mobile Phase A 0.1% formic acid in water
Mobile Phase B 0.1% formic acid in acetonitrile
Gradient initial 0% B, 1 mins—5% B; 7 mins—98% B; 9 mins—98% B; 9.1 mins—5% B; 10 mins—5% B
Flow rate 18 mL/min
Injection volume 1000 uL
Method 2 Basic Conditions
Column Gemini NX C18, 5 um 21.2×100 mm
Temperature Ambient
Detection ELSD-MS
Mobile Phase A 0.1% diethylamine in water
Mobile Phase B 0.1% diethylamine in acetonitrile
Gradient initial 0% B, 1 mins—5% B; 7 mins—98% B; 9 mins—98% B; 9.1 mins—5% B; 10 mins—5% B
Flow rate 18 mL/min
Injection volume 1000 uL Example 1

5-[5-(7-Ethyl-7H-imidazo[4,5-c]pyridazin-4-yl)-2-fluorophenyl]-6-methoxy-2-methyl-2,3-dihydro-1H-isoindol-1-one

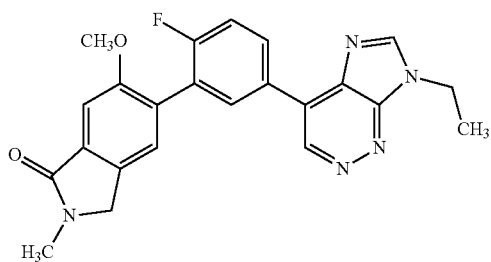

To a solution of 6-methoxy-2-methyl-5-(4,4,5,5-tetramethyl-1,3,2-dioxaborolan-2-yl)isoindolin-1-one (Preparation 23, 3.00 g, 9.90 mmol) and 4-(3-bromo-4-fluorophenyl)-7-ethyl-7H-imidazo[4,5-c]pyridazine (Preparation 5, 2.86 g, 8.91 mmol) in 1,4-dioxane (180 mL) and water (50 mL) at room temperature was added potassium carbonate (3.4 g, 24.7 mmol). The solution was degassed with nitrogen for 30 minutes before tetrakis(triphenylphosphine)palladium(0) (0.57 g, 4.95 mmol) was added and the reaction heated to 110° C. After 62 hours the reaction was cooled to room temperature and diluted with ethyl acetate (150 mL). The organic layer was washed with ammonium chloride solution (2×150 mL), brine (150 mL), dried over sodium sulfate, filtered and concentrated in vacuo. The crude residue was dissolved in dichloromethane (15 mL) and purified through an SCX column eluting initially with DCM:MeOH 150 mL:400 mL followed by aqueous ammonium hydroxide in methanol (0.880 M; 200 mL) to afford a yellow solid. The solid was triturated in methanol (50 mL), filtered, washed with methanol (150 mL) and air dried to afford a colourless solid (1.30 g). The mother liquor was concentrated in vacuo, triturated in methanol (20 mL), filtered, washed with methanol (50 mL) and air dried to afford a colourless solid (0.21 g). The solids were combined to afford the title compound (1.51 g, 37%).

$^1$H NMR (400 MHz, CDCl$_3$): δ ppm 1.70 (t, 3H), 3.24 (s, 3H), 3.89 (s, 3H), 4.39 (s, 2H), 4.58 (q, 2H), 7.36 (t, 1H), 7.42 (s, 1H), 7.47 (s, 1H), 8.21 (dd, 1H), 8.29-8.33 (m, 2H), 9.39 (s, 1H).

$^{19}$F NMR (400 MHz, CDCl$_3$): δ ppm −110.37
MS m/z 418 [M+H]$^+$

Example 2

5-{2-Fluoro-5-[7-(propan-2-yl)-7H-imidazo[4,5-c]pyridazin-4-yl]phenyl}-2-methyl-2, 3-dihydro-1H-isoindol-1-one

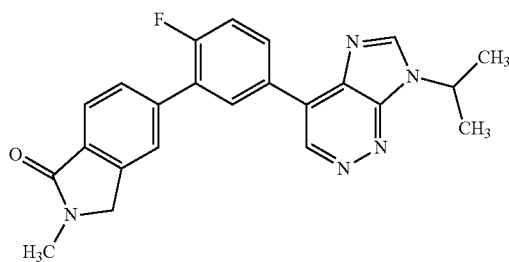 [SMILES: CC(C)n1cnc2c(-c3ccc(F)c(-c4ccc5c(c4)CN(C)C5=O)c3)cnnc21]

A solution of 4-(3-chloro-4-fluorophenyl)-7-(propan-2-yl))-7H-imidazo[4,5-c]pyridazine (Preparation 9, 1.92 g, 6.60 mmol), (2-methyl-1-oxoisoindolin-5-yl)boronic acid (PCT Int Appl 2010 128324, 1.39 g, 7.26 mmol), Cs$_2$CO$_3$ (4.30 g, 13.2 mmol) in water (25 mL) and dioxane (70 mL) was degassed with nitrogen for 30 minutes. Dichloro[1,1'-bis(di-tert-butylphosphino)]ferrocene palladium (II) (341 mg, 0.523 mmol) was added and the reaction heated to 80° C. for 3 hours. The reaction was cooled and diluted with water (50 mL) then extracted with EtOAc (3×100 mL) and DCM (100 mL). The combined organic extracts were concentrated in vacuo and purified by silica gel column chromatography eluting with 80-100% EtOAc in DCM to 5% MeOH in EtOAc. The resulting product was then triturated twice with MeCN (50 mL) to afford the title compound as a pale pink solid (1.16 g, 45%).

$^1$H NMR (400 MHz, CDCl$_3$): δ ppm 1.77 (d, 6H), 3.24 (s, 3H), 4.46 (s, 2H), 5.24 (m, 1H), 7.37 (m, 1H), 7.70-7.73 (m, 2H), 7.94 (d, 1H), 8.21 (m, 1H), 8.33 (s, 1H), 8.37 (m, 1H), 9.38 (s, 1H).

MS m/z 402 [M+H]$^+$

Unless otherwise specified, the compounds of the Examples that follow were prepared according to the method described for Example 1 using the appropriate aryl halide (compounds of general formulae (II), (VIII), (IX), (XV) and aryl boronic acid/ester (compounds of general formulae (V), (XV), (X), (XVI) with either sodium, potassium or cesium carbonate as base and one of the Purification Methods (PM) described below:

Purification Method A:
   Silica gel column chromatography eluting with 0-20% MeOH in DCM Purification Method B:
   Preparative HPLC Purification Method C:
   Preparative TLC eluting with 2% MeOH in DCM

| Example | | |
|---|---|---|
| | 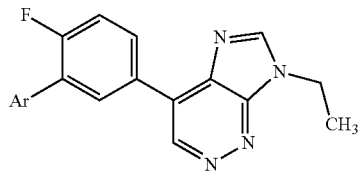 | |
| 3 | 5-[5-(7-Ethyl-7H-imidazo[4,5-c]pyridazin-4-yl)-2-fluorophenyl]-2-methyl-2,3-dihydro-1H-isoindol-1-one | |
| | 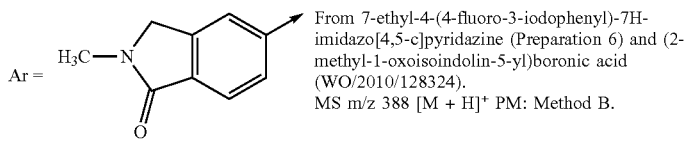 | From 7-ethyl-4-(4-fluoro-3-iodophenyl)-7H-imidazo[4,5-c]pyridazine (Preparation 6) and (2-methyl-1-oxoisoindolin-5-yl)boronic acid (WO/2010/128324).<br>MS m/z 388 [M + H]$^+$ PM: Method B. |
| 4 | 5'-(7-Ethyl-7H-imidazo[4,5-c]pyridazin-4-yl)-2'-fluoro-N-methylbiphenyl-3-carboxamide | |
| | 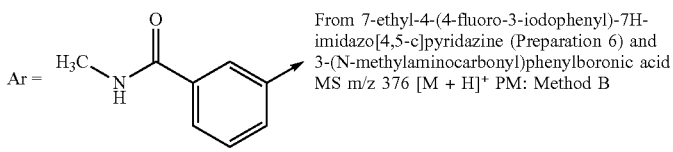 | From 7-ethyl-4-(4-fluoro-3-iodophenyl)-7H-imidazo[4,5-c]pyridazine (Preparation 6) and 3-(N-methylaminocarbonyl)phenylboronic acid<br>MS m/z 376 [M + H]$^+$ PM: Method B |
| 5 | 6-[5-(7-Ethyl-7H-imidazo[4,5-c]pyridazin-4-yl)-2-fluorophenyl]-2-methyl-2,3-dihydro-1H-isoindol-1-one | |
| | 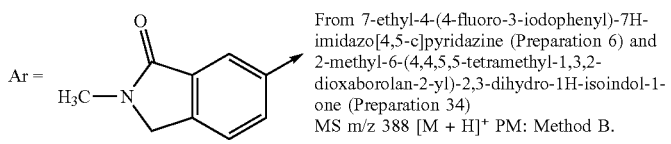 | From 7-ethyl-4-(4-fluoro-3-iodophenyl)-7H-imidazo[4,5-c]pyridazine (Preparation 6) and 2-methyl-6-(4,4,5,5-tetramethyl-1,3,2-dioxaborolan-2-yl)-2,3-dihydro-1H-isoindol-1-one (Preparation 34)<br>MS m/z 388 [M + H]$^+$ PM: Method B. |
| 6 | 6-[5-(7-Ethyl-7H-imidazo[4,5-c]pyridazin-4-yl)-2-fluorophenyl]-2,3-dihydro-1H-isoindol-1-one | |
| | 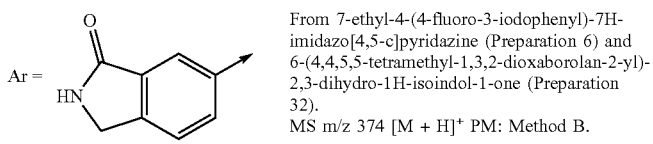 | From 7-ethyl-4-(4-fluoro-3-iodophenyl)-7H-imidazo[4,5-c]pyridazine (Preparation 6) and 6-(4,4,5,5-tetramethyl-1,3,2-dioxaborolan-2-yl)-2,3-dihydro-1H-isoindol-1-one (Preparation 32).<br>MS m/z 374 [M + H]$^+$ PM: Method B. |

| | | |
|---|---|---|
| 7 | 5'-(7-Ethyl-7H-imidazo[4,5-c]pyridazin-4-yl)-2',6-difluoro-N,N-dimethylbiphenyl-3-carboxamide 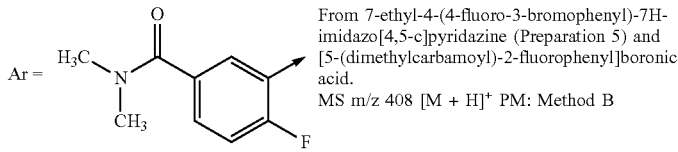 | From 7-ethyl-4-(4-fluoro-3-bromophenyl)-7H-imidazo[4,5-c]pyridazine (Preparation 5) and [5-(dimethylcarbamoyl)-2-fluorophenyl]boronic acid.<br>MS m/z 408 [M + H]+ PM: Method B |
| | 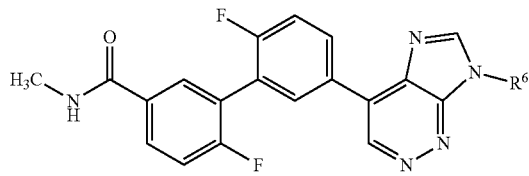 | |
| 8 | 5'-(7-Cyclopropyl-7H-imidazo[4,5-c]pyridazin-4-yl)-2',6-difluoro-N-methyl-biphenyl-3-carboxamide 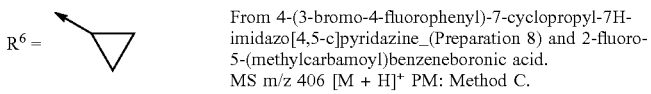 | From 4-(3-bromo-4-fluorophenyl)-7-cyclopropyl-7H-imidazo[4,5-c]pyridazine_(Preparation 8) and 2-fluoro-5-(methylcarbamoyl)benzeneboronic acid.<br>MS m/z 406 [M + H]+ PM: Method C. |
| 9 | 5'-(7-Ethyl-7H-imidazo[4,5-c]pyridazin-4-yl)-2',6-difluoro-N-methylbiphenyl-3-carboxamide 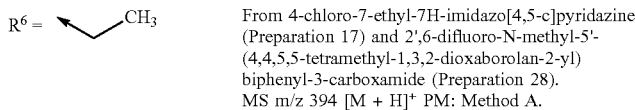 | From 4-chloro-7-ethyl-7H-imidazo[4,5-c]pyridazine (Preparation 17) and 2',6-difluoro-N-methyl-5'-(4,4,5,5-tetramethyl-1,3,2-dioxaborolan-2-yl)biphenyl-3-carboxamide (Preparation 28).<br>MS m/z 394 [M + H]+ PM: Method A. |

Example 10

5-[5-(7-Cyclopropyl-7H-imidazo[4,5-c]pyridazin-4-yl)-2-fluorophenyl]-2-methyl-2,3-dihydro-1H-isoindol-1-one

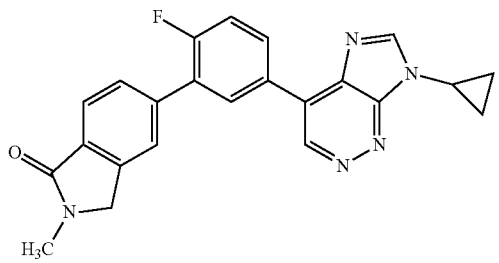 [SMILES: CN1Cc2cc(-c3cc(-c4cnnc5c4ncn5C4CC4)ccc3F)ccc2C1=O]

4-(3-bromo-4-fluorophenyl)-7-cyclopropyl-7H-imidazo[4,5-c]pyridazine (Preparation 8, 70 mg, 0.21 mmol), (2-methyl-1-oxoisoindolin-5-yl)boronic acid (PCT Int Appl 2010 128324, 60 mg, 0.32 mmol), dichloro[1,1'-bis(di-tert-butylphosphino)]ferrocene palladium (II) (14 mg, 0.021 mmol) and cesium carbonate (137 mg, 0.42 mmol) in DMF (2 mL) was degassed with nitrogen followed by heating to 95° C. for 18 hours. The reaction was cooled and filtered through silica gel eluting with EtOAc. The filtrate was concentrated in vacuo and the residue purified using reverse phase column chromatography eluting with 3-60% (0.1% formic acid in acetonitrile) in (0.1% formic acid in water) to afford the title compound as a white solid (15 mg, 18%).

$^1$H NMR (400 MHz, CDCl$_3$): δ ppm 1.25-1.28 (m, 2H), 1.34-1.39 (m, 2H), 3.23 (s, 3H), 3.70-3.78 (m, 1H), 4.48 (s, 2H), 7.40 (t, 1H), 7.69-7.72 (m, 2H), 7.94 (d, 1H), 8.17-8.20 (m, 1H), 8.28 (s, 1H), 8.35 (d, 1H), 9.40 (s, 1H).

MS m/z 400 [M+H]+

Example 11

5'-(7-Cyclopropyl-7H-imidazo[4,5-c]pyridazin-4-yl)-2'-fluoro-N-methylbiphenyl-4-carboxamide

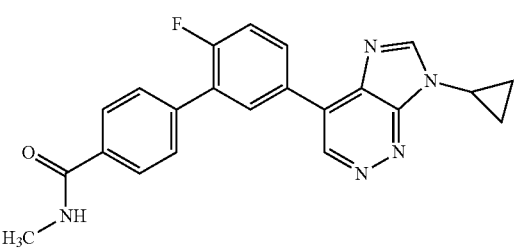 [SMILES: CNC(=O)c1ccc(-c2cc(-c3cnnc4c3ncn4C3CC3)ccc2F)cc1]

7-cyclopropyl-4-[4-fluoro-3-(4,4,5,5-tetramethyl-1,3,2-dioxaborolan-2-yl)phenyl]-7H-imidazo[4,5-c]pyridazine (Preparation 3, 100 mg, 0.26 mmol) and 4-bromo-N-methylbenzamide (84 mg, 0.39 mmol) were dissolved in DIPEA (1 mL) and DMF (5 mL) and degassed with nitrogen. Dichloro[1,1'-bis(di-tert-butylphosphino)]ferrocene palladium (II) (50 mg, 0.10 mmol) was added and the reaction heated to 90° C. for 18 hours. The reaction was cooled, diluted with EtOAc (10 mL), washed with water (3×10 mL), dried over Na$_2$SO$_4$ and concentrated in vacuo. The residue was purified using silica gel column chromatography eluting with a gradient of 70-100% EtOAc in heptanes followed by trituration with ether to afford the title compound as an orange solid (28 mg, 28%).

MS m/z 388 [M+H]+

Example 12

2'-Fluoro-5'-[7-(propan-2-yl)-7H-imidazo[4,5-c]pyridazin-4-yl]biphenyl-4-carboxamide

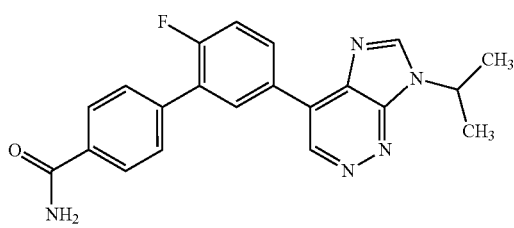 [SMILES: CC(C)n1cnc2c(-c3ccc(F)c(-c4ccc(C(N)=O)cc4)c3)cnnc21]

To a solution of 2'-fluoro-5'-(4,4,5,5-tetramethyl-1,3,2-dioxaborolan-2-yl)biphenyl-4-carboxamide (Preparation 30, 170 mg, 0.5 mmol) and 4-chloro-7-isopropyl-7H-imidazo[4,5-c]pyridazine (Preparation 14, 98 mg, 0.5 mmol) in dioxane (3 mL) was added a 2M solution of sodium carbonate in water (0.747 mL) followed by [1,1'-bis(diphenylphosphino)ferrocene]dichloropalladium (II) complex with dichloromethane (14 mg, 0.0170 mmol). The reaction was degassed before heating to 90° C. under microwave irradiation for 15 minutes. The reaction was cooled, diluted with EtOAc, dried over sodium sulphate and concentrated in vacuo. The residue was purified using silica gel column chromatography eluting with 10% MeOH in DCM to afford the title compound as a yellow solid (50 mg, 27%).

$^1$H NMR (400 MHz, CDCl$_3$): δ ppm 1.67 (d, 6H), 5.12 (m, 1H), 6.05 (br s, 1H), 7.00 (br s, 1H), 7.25 (m, 1H), 7.62 (m, 2H), 7.90 (m, 2H), 8.04-8.22 (m, 1H), 8.18-8.37 (m, 2H), 9.27 (s, 1H).

MS m/z 376 [M+H]$^+$

Example 13

5'-(7-Ethyl-7H-imidazo[4,5-c]pyridazin-4-yl)-2'-fluoro-N,N-dimethylbiphenyl-4-carboxamide

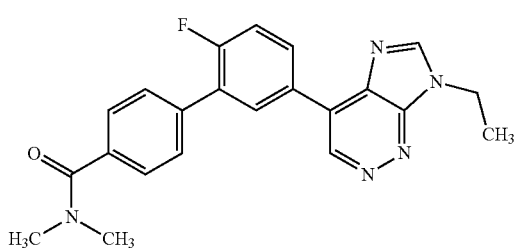

A solution of 7-ethyl-4-(4-fluoro-3-chlorophenyl)-7H-imidazo[4,5-c]pyridazine (Preparation 7, 200 mg, 0.72 mmol), 4-(dimethylcarbamoyl)phenylboronic acid (195 mg, 1.01 mmol), palladium(II)acetate (16 mg, 0.072 mmol), 2-dicyclohexylphosphino-2',4',6'-triisopropylbiphenyl (68 mg, 0.14 mmol) and potassium carbonate (300 mg, 2.16 mmol) were dissolved in 2-methyl-2-butanol (10 mL) and water (5 mL). The reaction was degassed with argon before heating to reflux for 18 hours. The reaction was cooled, diluted with EtOAc, filtered through celite and concentrated in vacuo. The residue was eluted through an SCX cartridge followed by purification using reverse phase column chromatography eluting with a gradient of 5-95% acetonitrile in 0.1% formic acid in water to afford the title compound as a colourless foam (22 mg, 8%).

$^1$H NMR (400 MHz, CDCl$_3$): δ ppm 1.66 (t, 3H), 3.08 (d, 6H), 4.57 (q, 2H), 7.34 (t, 1H), 7.52 (d, 2H), 7.66 (d, 2H), 8.18 (m, 1H), 8.29 (s, 1H), 8.32 (dd, 1H), 9.36 (s, 1H).

MS m/z 390 [M+H]$^+$

Library Protocol 1

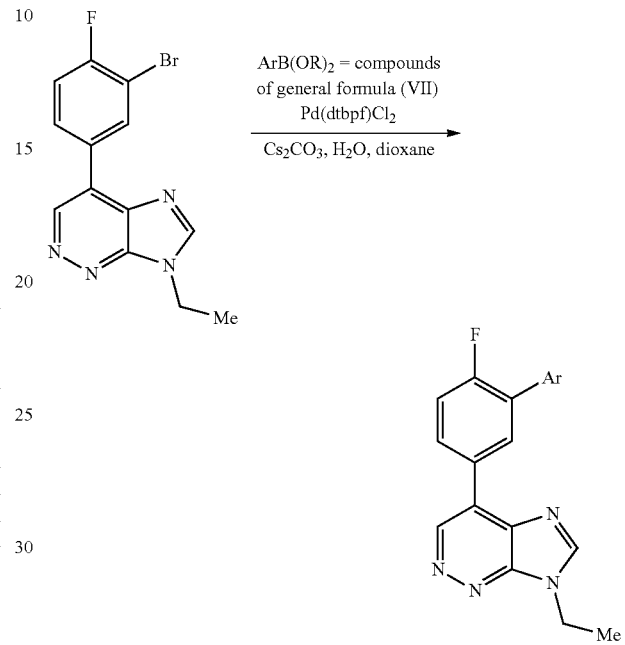

To a 0.282M solution of 4-(3-bromo-4-fluoro-phenyl)-7-ethyl-7H-imidazo[4,5-c]pyridazine (Preparation 5, 400 μL, 75 μmol) in dioxane was added a 0.188M solution of compounds of general formula (VII) (400 μL, 113 μmol) in dioxane. Water (100 μL), and cesium carbonate (48.87 mg, 150 μmol) were added and the mixture degassed with nitrogen. 1,1'-bis(di-tert-butylphosphino)ferrocene palladium dichloride (2.5 mg, 3.75 μmol) was added, the reaction degassed with nitrogen and heated to 120° C. for 16 hours. The reaction was cooled, filtered and concentrated in vacuo. The residue was purified using either preparative HPLC Method A or B as described below.

Preparative HPLC Method A:

Grace Vydac C18 250×20 mm×5 um eluting with a gradient of between 29-64% acetonitrile in 0.1% TFA in water. Gradient time: 11 mins, hold time: 1.5 mins, flow rate: 28 mL/min. Products were isolated as the TFA salt.

Preparative HPLC Method B:

Phenomenex Gemini C18 eluting with a gradient of 29-59% acetonitrile in ammonium hydroxide (pH=10). Gradient time: 9 mins, hold time: 1 min, flow rate: 25 mL/min.

LCMS QC:

A: 0.0375% TFA in water; B: 0.01875% TFA in MeCN
Column: Welch XB-C18 2.1×50 mm 5 μm
Gradient: From 99% [A] and 1% [B] to 95% [A] and 5% [B] in 1 min, further to 100% [B] in 4.0 min and finally back to initial condition in 4.30 min, 0.8 mL/minflow rate Examples 14-19 were prepared according to Library Protocol 1 using 4-(3-bromo-4-fluoro-phenyl)-7-ethyl-7H-imidazo[4,5-c]pyridazine (Preparation 5) and compounds of formula (VII).

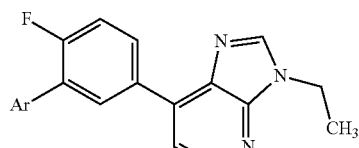

| Example | | |
|---|---|---|
| 14 | 5'-(7-Ethyl-7H-imidazo[4,5-c]pyridazin-4-yl)-2'-fluorobiphenyl-4-carboxamide | |
| | 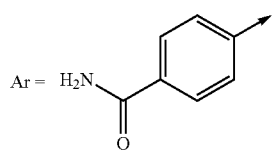 | Using (4-aminocarbonylphenyl)boronic acid<br>MS m/z 362 [M + H]$^+$ PM: Method B. |
| 15 | 5'-(7-Ethyl-7H-imidazo[4,5-c]pyridazin-4-yl)-2'-fluorobiphenyl-3-carboxamide trifluoroacetate salt | |
| | 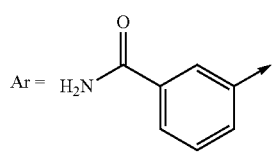 | Using (3-aminocarbonyl)phenylboronic acid<br>MS m/z 362 [M + H]$^+$ PM: Method A. |
| 16 | 5'-(7-Ethyl-7H-imidazo[4,5-c]pyridazin-4-yl)-2'-fluoro-N-methylbiphenyl-4-carboxamide trifluoroacetate salt | |
| | 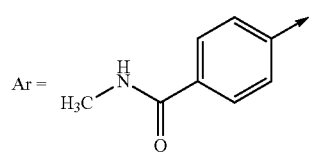 | Using 4-(N-methylaminocarbonyl)phenylboronic acid<br>MS m/z 376 [M + H]$^+$ PM: Method A. |
| 17 | 5'-(7-Ethyl-7H-imidazo[4,5-c]pyridazin-4-yl)-2',3-difluoro-N,N-dimethylbiphenyl-4-carboxamide trifluoroacetate salt | |
| | 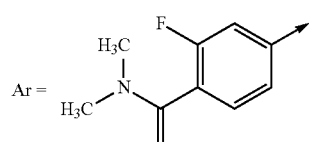 | Using 4-(N-dimethylaminocarbonyl)-3-fluoro-phenylboronic acid<br>MS m/z 408 [M + H]$^+$ PM: Method A. |
| 18 | 5'-(7-Ethyl-7H-imidazo[4,5-c]pyridazin-4-yl)-2'-fluoro-N-(propan-2-yl)biphenyl-4-carboxamide trifluoroacetate salt | |
| | 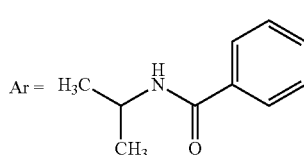 | Using 4-(N-isopropylaminocarbonyl)phenyl-boronic acid<br>MS m/z 404 [M + H]$^+$ PM: Method A |
| 19 | 5'-(7-Ethyl-7H-imidazo[4,5-c]pyridazin-4-yl)-2',5-difluoro-N-methylbiphenyl-3-carboxamide trifluoroacetate salt | |
| | 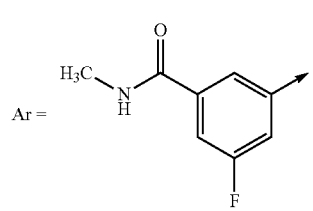 | Using 3-fluoro-5-(methylcarbamoyl)phenyl-boronic acid<br>MS m/z 394 [M + H]$^+$ PM: Method A. |

Library Protocol 2

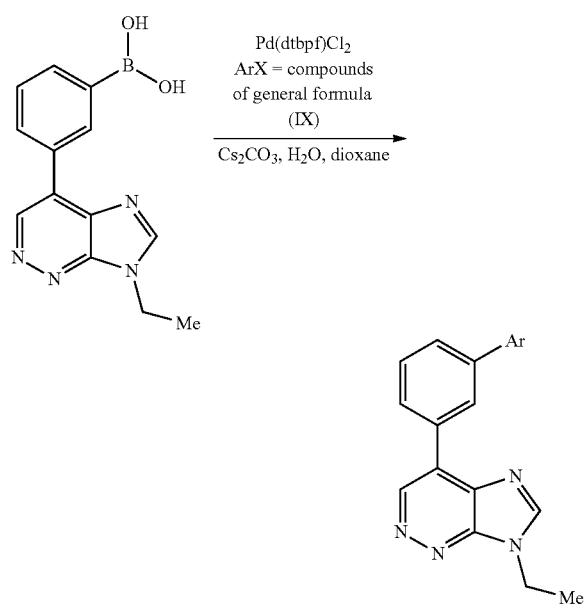

To compounds of general formula (IX) (100 μmol) was added a 0.16M solution of 3-(7-ethyl-7H-imidazo[4,5-c]pyridazin-4-yl)benzene boronic acid (Preparation 1, 100 μmol) in dioxane/DMSO (V:V=3.5:1) followed by a 2.22M solution of cesium carbonate (112.5 μL, 250 μmol) in water. The mixture was degassed with nitrogen and 1,1'-bis(di-tert-butylphosphino)ferrocene palladium dichloride (5 μmol) added followed by a further degassing with nitrogen. The reaction was heated to 110° C. for 16 hours, cooled, concentrated in vacuo and purified using preparative HPLC using the method below.
Preparative HPLC:
Boston Symmetrix ODS-H 150 mm×30 mm×5 um eluting with a gradient of 31-61% acetonitrile in 0.225% formic acid in water. Gradient time: 10 mins, hold time: 1.5 mins, flow rate: 25 mL/min. Products were isolated as the TFA salt.
LCMS QC:
A: 0.0375% TFA in water; B: 0.01875% TFA in MeCN
Column: Welch XB-C18 2.1×50 mm 5 μm
Gradient: From 99% [A] and 1% [B] to 95% [A] and 5% [B] in 1 min, further to 100% [B] in 4.0 min and finally back to initial condition in 4.30 min, 0.8 mL/minflow rate
Example 20 was prepared according to Library Protocol 2 using 3-(7-ethyl-7H-imidazo[4,5-c]pyridazin-4-yl)benzene boronic acid (Preparation 1) and compounds of general formula (IX).

| Example | | |
|---|---|---|
| | 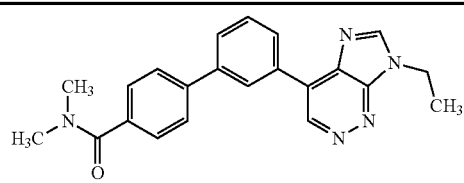 | |
| 20 | 5'-(7-Ethyl-7H-imidazo[4,5-c]pyridazin-4-yl)-N,N-dimethyl-biphenyl-4-carboxamide trifluoroacetate salt<br>Using 4-bromo-N,N-dimethylbenzamide<br>MS m/z 372 [M + H]⁺ | |

Example 21

5'-(7-Ethyl-7H-imidazo[4,5-c]pyridazin-4-yl)-2'-fluoro-2-methoxy-N-methylbiphenyl-4-carboxamide

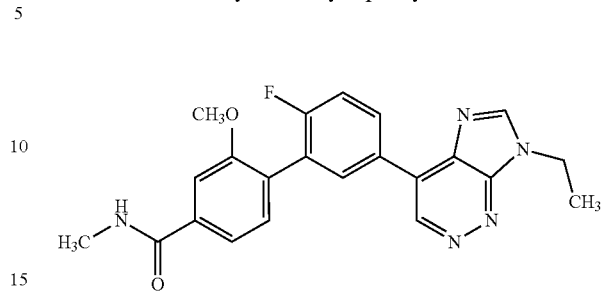

Methyl 5'-(7-ethyl-7H-imidazo[4,5-c]pyridazin-4-yl)-2'-fluoro-2-methoxybiphenyl-4-carboxylate (Preparation 10, 60 mg, 0.148 mmol) was dissolved in methanol (3 mL) and a solution of methylamine (33% w/v) in EtOH (1 mL) was added. The reaction was heated to 75° C. in a Reactivial™ for 18 hours before cooling and concentrating in vacuo. The residue was purified using preparative HPLC to afford the title compound (20 mg, 76%).
¹H NMR (400 MHz, CDCl₃): δ ppm 1.69 (t, 3H), 3.05 (d, 3H), 3.89 (s, 3H), 4.55-4.60 (q, 2H), 6.22 (br s, 1H), 7.30-7.42 (m, 3H), 7.54 (s, 1H), 8.19-8.23 (m, 1H), 8.27-8.32 (m, 2H), 9.38 (s, 1H).
MS m/z 406 [M+H]⁺

Example 22

5'-(7-Ethyl-7H-imidazo[4,5-c]pyridazin-4-yl)-2'-fluoro-2-methoxy-N,N-dimethylbiphenyl-4-carboxamide

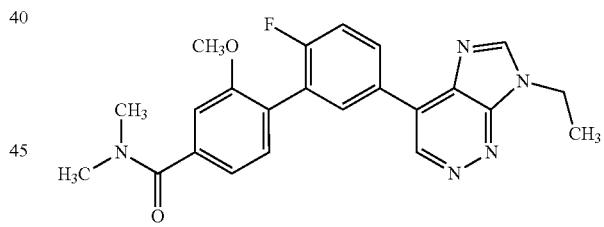

5'-(7-Ethyl-7H-imidazo[4,5-c]pyridazin-4-yl)-2'-fluoro-2-methoxybiphenyl-4-carboxylic acid (Preparation 10, 125 mg, 0.319 mmol) was suspended in DCM (4 mL) and DMF (1 μL). Oxalyl chloride (150 μL, 1.77 mmol) was added and the reaction stirred at room temperature for 2.5 hours before concentrating in vacuo, azeotroping with DCM. The residue was added to an ice-cooled mixture of dimethylamine hydrochloride (70 mg, 0.859 mmol) and diisopropylethylamine (300 μL, 1.72 mmol) in DCM (4 mL), and the reaction was allowed to stir, warming to room temperature for 48 hours. The reaction was concentrated in vacuo and the residue purified using preparative HPLC to afford the title compound (84 mg, 64%).
¹H NMR (400 MHz, CDCl₃): δ ppm 1.70 (t, 3H), 3.08 (s, 3H), 3.15 (s, 3H), 3.85 (s, 3H), 4.56-4.61 (q, 2H), 7.06-7.11 (m, 2H), 7.32-7.39 (m, 2H), 8.20-8.24 (m, 1H), 8.28-8.33 (m, 1H), 8.37 (s, 1H), 9.41 (s, 1H).
MS m/z 420 [M+H]⁺

Example 23

5'-(7-Ethyl-7H-imidazo[4,5-c]pyridazin-4-yl)-2'-fluoro-6-methoxy-N,N-dimethylbiphenyl-3-carboxamide

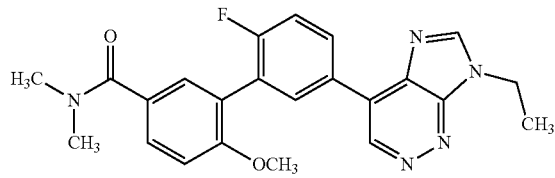 [SMILES: CCn1cnc2c(-c3ccc(F)c(-c4cc(C(=O)N(C)C)ccc4OC)c3)cnnc21]

5'-(7-Ethyl-7H-imidazo[4,5-c]pyridazin-4-yl)-2'-fluoro-2-methoxybiphenyl-4-carboxylic acid (Preparation 10, 50 mg, 0.127 mmol), EDCI (32 mg, 0.166 mmol), HOBt (20 mg, 0.133 mmol) and NMM (26 mg, 0.254 mmol) in dioxane (2 mL) were stirred at room temperature for 1 hour. Dimethylamine in THF (1 mL) was added and the reaction was stirred at room temperature for 18 hours. The reaction was concentrated in vacuo, and purified using preparative HPLC to afford the title compound.

$^1$H NMR (400 MHz, CDCl$_3$): δ ppm 1.69 (t, 3H), 3.12 (s, 6H), 3.86 (s, 3H), 4.58 (q, 2H), 7.04 (d, 1H), 7.34 (t, 1H), 7.48 (s, 1H), 7.55 (m, 1H), 8.22 (m, 1H), 8.24-8.32 (m, 2H), 9.39 (s, 1H).

MS m/z 420 [M+H]$^+$

Preparation 1

3-(7-Ethyl-7H-imidazo[4,5-c]pyridazin-4-yl)benzeneboronic acid

To a room temperature solution of 2-[3-(7-ethyl-7H-imidazo[4,5-c]pyridazin-4-yl)-phenyl]-2,3-dihydro-1H-1,3-diaza-2-boraphenalene (Preparation 2, 10.5 g, 26.9 mmol) in THF (400 mL) was added 5N hydrogen chloride aqueous solution (110 mL, 0.55 mol) and the resultant reaction mixture stirred at reflux for 16 hours. After cooling to room temperature, the reaction mixture was filtered and the filtrate was neutralized with potassium carbonate until pH=6. The resulting precipitate was filtered and the filter cake was washed with a small quantity of EtOAc. The collected solid was dried under vacuum to afford the title compound as an off white solid (4.5 g, 62%). Taken directly on to the next step.

Preparation 2

2-[3-(7-Ethyl-7H-imidazo[4,5-c]pyridazin-4-yl phenyl]-2,3-dihydro-1H-1,3-diaza-2-boraphenalene A room temperature solution of 2-[3-(4,4,5,5-tetramethyl-[1,3,2]dioxaborolan-2-yl)phenyl]-2,3-dihydro-1H-1,3-diaza-2-boraphenalene (Preparation 31, 7.8 g, 21.1 mmol), 4-chloro-7-ethyl-7H-imidazo[4,5-c]pyridazine (Preparation 17, 2.6 g, 14.1 mmol) and cesium carbonate (13.8 g, 42.3 mmol) in dioxane (160 mL) and water (13 mL) was degassed. 1,1'-bis(di-tert-butylphosphino) ferrocene palladium dichloride (0.91 g, 1.4 mmol) was then added in one portion, the reaction mixture was degassed and the resultant solution stirred at reflux for 16 hours. The reaction mixture was cooled to room temperature then filtered and concentrated in vacuo. The residue was purified by silica gel column chromatography eluting with DCM:MeOH, 50:1 to afford the title compound as a yellow solid (4.6 g, 84%).

$^1$H NMR (400 MHz, CDCl$_3$): δ ppm 1.69 (t, 3H), 4.58 (q, 2H), 6.23 (s, 2H), 6.44 (d, 2H), 7.06 (d, 2H), 7.12-7.16 (m, 2H), 7.61-7.65 (m, 1H), 7.76 (d, 1H), 8.21 (d, 1H) 8.28 (s, 1H), 8.45 (s, 1H), 9.39 (s, 1H).

Preparation 3

7-Cyclopropyl-4-[4-fluoro-3-(4,4,5,5-tetramethyl-1,3,2-dioxaborolan-2-yl)phenyl]-7H-imidazo[4,5-c]pyridazine A mixture of 4-(3-bromo-4-fluorophenyl)-7-cyclopropyl-7H-imidazo[4,5-c]pyridazine (Preparation 8, 820 mg, 2.461 mmol), bispinacolatodiboron (938 mg, 3.692 mmol) and potassium acetate (483 mg, 4.922 mmol) in dioxane (20 mL) was degassed with nitrogen before the addition of 1,1'-bis(di-phenylphosphino)ferrocene palladium (II) dichloride (201 mg, 0.246 mol). The reaction was heated to 100° C. for 3 hours before cooling and filtering through celite, washing with EtOAc. The filtrate was concentrated in vacuo and purified using silica gel column chromatography eluting with 0-2% MeOH in EtOAc followed by trituration with EtOAc to afford the title compound as an off-white solid (510 mg, 55%).

$^1$H NMR (400 MHz, CDCl$_3$): δ ppm 1.25-1.34 (m, 4H), 1.39 (s, 12H), 3.67-3.73 (m, 1H), 7.21-7.26 (s, 1H), 8.25 (s, 1H), 8.40-8.44 (m, 2H), 9.40 (s, 1H).

MS m/z 299 [M+H]$^+$ Boronic acid, MS m/z 381 [M+H]$^+$ Boronate ester

Preparation 4

7-Ethyl-4-[4-fluoro-3-(4,4,5,5-tetramethyl-1,3,2-dioxaborolan-2-yl)phenyl]-7H-imidazo[4,5-c]pyridazine The title compound was prepared according to Preparation 3 using 4-(3-bromo-4-fluoro-phenyl)-7-ethyl-7H-imidazo[4,5-c]pyridazine (Preparation 5) as a pale brown solid (2.47 g, 62%).

$^1$H NMR (400 MHz, CDCl$_3$): δ ppm 1.36 (s, 12H), 1.66 (t, 3H), 4.55 (q, 2H), 7.19-7.24 (m, 1H), 8.25 (s, 1H), 8.41-8.44 (m, 2H), 9.36 (s, 1H).

Preparation 5

4-(3-Bromo-4-fluoro-phenyl)-7-ethyl-7H-imidazo[4,5-c]pyridazine

Concentrated sulphuric acid (66 g, 0.67 mol) was carefully added to 7-ethyl-4-(4-fluorophenyl)-7H-imidazo[4,5-c]pyridazine (Preparation 12, 2.3 g, 9.5 mmol) surrounded by an ice bath, and the resultant reaction mixture was gently stirred at room temperature until a homogeneous solution was observed. To this solution was added 1,3-dibromo-5,5-dimethylhydantoin (2.7 g, 9.5 mmol) portion-wise, and stirring was continued at 0° C. for 2 hours. The reaction mixture was poured carefully into aqueous sodium bisulphite (200 mL), and then basified with an aqueous sodium hydroxide solution (2 M) to pH=8 keeping the temperature below 20° C. EtOAc (50 mL) was added and the layers were separated. The aqueous layer was extracted with EtOAc (2×50 mL). The combined organic phases were washed with saturated brine solution, dried over Na$_2$SO$_4$ and concentrated in vacuo. The residue was purified by silica gel column chromatography eluting with petroleum ether:DCM 1:1 followed by trituration with EtOAc to afford the title compound as a white solid (1.25 g, 41%).

$^1$H NMR (400 MHz, CDCl$_3$): δ ppm 1.70 (t, 3H), 4.58 (q, 2H), 7.26-7.34 (m, 1H), 8.16-8.25 (m, 1H), 8.31 (s, 1H), 8.44-8.50 (m, 1H), 9.32 (s, 1H).

MS m/z 323 [M$^{81}$Br+H]$^+$

The title compound may also be prepared according to the following preparation:

To a mixture of 2-(3-bromo-4-fluorophenyl)-4,4,5,5-tetramethyl-1,3,2-dioxaborolane (Preparation 13, 6.1 g, 16.28 mmol) in dioxane (60 mL) was added 4-iodo-7-ethyl-7H-imidazo[4,5-c]pyridazine (Preparation 15, 0.5 g, 13.28 mmol) and sodium carbonate (4.2 g, 39.8 mmol). The mixture was degassed and recharged with nitrogen. Tetrakis (triphenylphosphine)palladium(0) (1.5 g, 1.3 mmol) was added and the mixture heated to 80° C. for 24 hours under a nitrogen atmosphere. The mixture was diluted with ethyl acetate (200 mL) and washed with saturated ammonium chloride solution (400 mL), water and brine (200 mL each). The organic layer was evaporated and the resulting brown solid was triturated from acetonitrile to afford the title compound as white solid (2.2 g, 51%).

Preparation 6

7-Ethyl-4-(4-fluoro-3-iodophenyl)-7H-imidazo[4,5-c]pyridazine

Concentrated sulphuric acid (10 mL) was carefully added to 7-ethyl-4-(4-fluorophenyl)-7H-imidazo[4,5-c]pyridazine (Preparation 12, 825 mg, 2.4 mmol) surrounded by an ice bath, and the resultant reaction mixture was gently stirred at room temperature until a homogeneous solution was observed. To this was added 1,3-diiodo-5,5-dimethylhydantoin (1.36 g, 3.58 mmol) portion-wise, and stirring was continued for 5 minutes. The viscous mixture was then slowly poured into an aqueous sodium hydroxide solution (1M, 10 mL) at 0° C. with stirring. The black suspension slowly dissolved to give a blue solution. DCM (20 mL) was added and the layers were separated. The organic layer was washed with saturated aqueous sodium bisulfite solution (20 mL) then concentrated in vacuo. The residue was purified using silica gel column chromatography eluting with heptane:EtOAc 1:1 to 0:100 to afford the title compound as a white solid (1.19 g, 95%).

$^1$H-NMR (400 MHz, CDCl$_3$): δ ppm 1.70 (t, 3H), 4.58 (q, 2H), 7.25 (m, 1H), 8.19-8.23 (m, 1H), 8.29 (s, 1H), 8.65 (dd, 1H), 9.32 (s, 1H).

MS m/z 369 [M$^{127}$I+H]$^+$

Preparation 7

7-Ethyl-4-(4-fluoro-3-chlorophenyl)-7H-imidazo[4,5-c]pyridazine

4-Chloro-7-ethyl-7H-imidazo[4,5-c]pyridazine (Preparation 17, 1 g, 5.48 mmol), (3-chloro-4-fluorophenyl)boronic acid (0.95 g, 5.48 mmol), tetrakis(triphenylphosphine)palladium(0) (633 mg, 0.548 mmol) and sodium carbonate (1.74 g, 16.44 mmol) were dissolved in dioxane (55 mL) and water (20 mL). The mixture was degassed with nitrogen for 10 minutes before heating to reflux and for 24 hours. The reaction was cooled and diluted with ethyl acetate before filtration through a pad of celite. The filtrate was evaporated under reduced pressure and the resultant residue was eluted through an SCX-2 cartridge to afford the title compound as a pale brown solid (1.52 g, 99%).

$^1$H NMR (400 MHz, CDCl$_3$): δ ppm 1.68 (t, 3H), 4.58 (q, 2H), 7.34 (t, 1H), 8.11 (m, 1H), 8.30 (s, 1H), 8.35 (dd, 1H), 9.32 (s, 1H).

MS m/z 277 [M$^{35}$Cl+H]$^+$

Preparation 8

4-(3-Bromo-4-fluorophenyl)-7-cyclopropyl-7H-imidazo[4,5-c]pyridazine

The title compound was prepared according to the method described for Preparation 5 using 7-cyclopropyl-4-(4-fluorophenyl)-7H-imidazo[4,5-c]pyridazine (Preparation 11, 450 mg, 1.77 mmol) and 1,3-dibromo-5,5-dimethylhydantoin (253 mg, 0.885 mmol) to afford a white solid (500 mg, 25%).

$^1$H NMR (400 MHz, DMSO-d$_6$): δ ppm 1.18-1.24 (m, 4H), 3.77-3.78 (m, 1H), 7.63 (t, 1H), 8.45-8.51 (m, 1H), 8.82-8.85 (m, 2H), 9.58 (s, 1H).

MS m/z 333 [M$^{79}$Br+H]$^+$

Preparation 9

4-(3-Chloro-4-fluorophenyl)-7-(propan-2-yl))-7H-imidazo[4,5-c]pyridazine

A solution of 4-chloro-7-isopropyl-7H-imidazo[4,5-c]pyridazine (Preparation 14, 1.04 g, 5.29 mmol), 3-chloro-4-fluorophenylboronic acid (1.01 g, 5.82 mmol) and cesium carbonate (3.45 g, 10.6 mmol) in dioxane/water (20 mL/7 mL) was degassed with nitrogen for 30 minutes. Tetrakis (triphenylphosphine)palladium(0) (305 mg, 0.265 mmol) was added and the reaction heated to 85° C. for 16 hours. The reaction was cooled, diluted with water (20 mL) and extracted into EtOAc (40 mL). The organic layer was concentrated in vacuo and purified using silica gel column chromatography eluting with 20% EtOAc in DCM to afford the title compound as an orange powder (1.12 g, 73%).

$^1$H NMR (400 MHz, CDCl$_3$): δ ppm 1.78 (d, 6H), 5.21 (m, 1H), 7.36 (t, 1H), 8.12 (m, 1H), 8.34-8.38 (m, 2H), 9.31 (s, 1H).

MS m/z 291 [M$^{35}$Cl+H]$^+$

Preparation 10

Methyl 5'-(7-ethyl-7H-imidazo[4,5-c]pyridazin-4-yl)-2'-fluoro-2-methoxybiphenyl-4-carboxylate and 5'-(7-ethyl-7H-imidazo[4,5-c]pyridazin-4-yl)-2'-fluoro-2-methoxybiphenyl-4-carboxylic acid 7-Ethyl-4-(4-fluoro-3-chlorophenyl)-7H-imidazo[4,5-c]pyridazine (Preparation 7, 200 mg, 0.723 mmol), methyl-3-methoxy-4-(4,4,5,5-tetramethyl-1,3,2-dioxaborolan-2-yl) benzoate (Preparation 29, 300 mg, 1.027 mmol) dicyclohexyl(2',4',6'-triisopropyl-[1,1'-biphenyl]-2-yl)phosphine (35 mg, 0.073 mmol), palladium (II) acetate (8 mg, 0.036 mmol) and potassium carbonate (280 mg, 2.029 mmol) were mixed in 2-methyl-2-butanol (6 mL) and water (3 mL) under nitrogen and heated to 110° C. for 18 hours. The reaction was cooled and partitioned between water (50 mL) and EtOAc (50 mL). The aqueous layer was separated and extracted further with EtOAc (10 mL).

The combined organic layers were dried over sodium sulphate and concentrated in vacuo. The residue was triturated with tert-butylmethylether (2 mL) to afford methyl 5'-(7-ethyl-7H-imidazo[4,5-c]pyridazin-4-yl)-2'-fluoro-2-methoxybiphenyl-4-carboxylate (125 mg, 43%).

$^1$H NMR (400 MHz, CDCl$_3$): δ ppm 1.69 (t, 3H), 3.89 (s, 3H), 3.96 (s, 3H), 4.55-4.61 (q, 2H), 7.35 (t, 1H), 7.43 (d, 1H), 7.69 (s, 1H), 7.75 (d, 1H), 8.22-8.24 (dd, 1H), 8.28-8.33 (m, 2H), 9.39 (s, 1H).

$^{19}$F NMR (376 MHz, CDCl$_3$): δ ppm −110.5

MS m/z 407 [M+H]$^+$

The combined aqueous layers were acidified with 1M aqueous citric acid to pH=4 and extracted with EtOAc twice (50 mL, 10 mL). The combined organic layers were dried over sodium sulphate and concentrated in vacuo. The residue was triturated with tert-butyldimethylether to afford 5'-(7-ethyl-7H-imidazo[4,5-c]pyridazin-4-yl)-2'-fluoro-2-methoxybiphenyl-4-carboxylic acid (125 mg, 43%).

$^1$H NMR (400 MHz, DMSO-d$_6$): δ ppm 1.53 (t, 3H), 3.82 (s, 3H), 4.46-4.52 (q, 2H), 7.46-7.53 (m, 2H), 7.62-7.68 (m, 2H), 8.44-8.49 (m, 2H), 8.85 (s, 1H), 9.54 (s, 1H).

$^{19}$F NMR (376 MHz, CDCl$_3$): δ ppm −111.5

MS m/z 393 [M+H]$^+$

Methyl 5'-(7-ethyl-7H-imidazo[4,5-c]pyridazin-4-yl)-2'-fluoro-2-methoxybiphenyl-4-carboxylate may also be prepared according to the following method:

A solution of 7-ethyl-4-[4-fluoro-3-(4,4,5,5-tetramethyl-1,3,2-dioxaborolan-2-yl)phenyl]-7H-imidazo[4,5-c]pyridazine (Preparation 4, 50 mg, 0.136 mmol) and methyl-3-bromo-4-methoxybenzoate (33 mg, 0.136 mmol) in DIPEA (0.4 mL) and DMF (2 mL) was degassed with nitrogen before the addition of bis (tri-tert-butylphosphine) palladium (0) (7 mg, 0.014 mmol) and heating to 90° C. for 18 hours. The reaction was cooled, diluted with EtOAc (20 mL) and washed with brine (20 mL). The organic layer was collected, concentrated in vacuo and purified using silica gel column chromatography eluting with EtOAc to afford the title compound.

5'-(7-ethyl-7H-imidazo[4,5-c]pyridazin-4-yl)-2'-fluoro-2-methoxybiphenyl-4-carboxylic acid may also be prepared according to the following method:

A mixture of methyl 5'-(7-ethyl-7H-imidazo[4,5-c]pyridazin-4-yl)-2'-fluoro-2-methoxybiphenyl-4-carboxylate (55 mg, 0.136 mmol) and LiOH (3.6 mg, 0.150 mmol) in THF (2 mL) and water (1 mL) was stirred at room temperature for 3 hours. Further LiOH (7.2 mg, 0.299 mmol) was added and the reaction stirred at room temperature for 18 hours. The reaction was concentrated in vacuo, dissolved in DCM and 1M HCl was added until pH=7. The organic layer was separated, the aqueous layer extracted with DCM, and the organic extracts combined, dried over Na$_2$SO$_4$ and concentrated in vacuo to afford the title compound.

Preparation 11

7-Cyclopropyl-4-(4-fluorophenyl)-7H-imidazo[4,5-c]pyridazine

To a room temperature solution of 4-chloro-7-cyclopropyl-7H-imidazo[4,5-c]pyridazine (Preparation 16, 1.00 g, 5.1 mmol) in dioxane (20 mL) was added 4-fluorobenzeneboronic acid (1.08 g, 7.71 mmol) and solution of Na$_2$CO$_3$ (2.72 g, 25.7 mmol in 12.8 mL water). The reaction mixture was degassed. Tetrakis(triphenylphosphine)palladium(0) (297 mg, 0.26 mmol) was then added and the mixture was heated to reflux for 16 hours. The solvent was removed in vacuo, the aqueous residue was filtered and purified by silica gel column chromatography eluting with EtOAc to afford the title compound as a red solid (949 mg, 73%).

$^1$H NMR (400 MHz, CDCl$_3$): δ ppm 1.25-1.37 (m, 4H), 3.69-3.73 (m, 1H), 7.24-7.28 (m, 2H), 8.19-8.23 (m, 2H), 8.25 (s, 1H), 9.36 (s, 1H).

MS m/z 255 [M+H]$^+$

Preparation 12

7-Ethyl-4-(4-fluorophenyl)-7H-imidazo[4,5-c]pyridazine

To a room temperature solution of 4-chloro-7-ethyl-7H-imidazo[4,5-c]pyridazine (Preparation 17, 9.6 g, 52.4 mmol) in dioxane (300 mL) was added 4-fluoro-benzeneboronic acid (8.8 g, 63 mmol) and an aqueous solution of Na$_2$CO$_3$ (1M, 260 mL, 262 mmol). The reaction mixture was degassed, tetrakis(triphenylphosphine)palladium(0) (1.2 g, 1.0 mmol) was added and the mixture heated to reflux for 4 hours. The organic solvent was removed in vacuo and the resulting aqueous mixture filtered. The filter cake was dried under vacuum to afford the title compound as a yellow solid (7 g, 55%).

$^1$H NMR (400 MHz, CDCl$_3$): δ ppm 1.62 (t, 3H), 4.50 (q, 2H), 7.19 (t, 2H), 8.14-8.18 (m, 2H), 8.21 (s, 1H), 9.27 (s, 1H).

Preparation 13

2-(3-Bromo-4-fluorophenyl)-4,4,5,5-tetramethyl-1,3,2-dioxaborolane

To a mixture of 2-bromo-1-fluoro-4-iodobenzene (5.0 g, 16.62 mmo) in dioxane (75 mL) was added bis(pinacolato)diboron (4.2 g, 16.62 mmol) and potassium carbonate (3.3 g, 33.2 mmol). The mixture was degassed and recharged with nitrogen. Bis(triphenylphosphine)palladium(II)dichloride (0.60 g, 0.83 mmol) was added and the mixture heated to 100° C. for 18 hours under a nitrogen atmosphere. The mixture was diluted with ethyl acetate (300 mL) and washed with saturated ammonium chloride solution, water and brine (200 mL each). The organic layer was evaporated to give the title compound as dark red oil (6.1 g) which was used without further purification.

$^1$H NMR (400 MHz, CDCl$_3$): δ ppm 1.33 (s, 12H), 7.10 (t, 1H), 7.72-7.65 (m, 1H), 8.00 (dd, 1H) ppm.

Preparation 14

4-Chloro-7-isopropyl-7H-imidazo[4,5-c]pyridazine

A solution of 5-chloro-N$^3$-isopropylpyridazine-3,4-diamine (Preparation 19, 14.4 mmol) in triethyl orthoformate (36 mL) was heated to 145° C. for 2.5 hours then allowed to cool. The solution was concentrated in vacuo and EtOAc (100 mL) added. The solution was filtered and the filtrate concentrated in vacuo. The crude residue was purified by silica gel column chromatography eluting with 50-100% EtOAc in Heptanes to afford the title compound as a light brown powder (1.04 g, 22% over 2 steps).

$^1$H NMR (400 MHz, CDCl$_3$): δ ppm 1.97 (d, 6H), 5.18 (m, 1H), 8.33 (s, 1H), 9.14 (s, 1H).

MS m/z 197 [M$^{35}$Cl+H]$^+$

Preparation 15

4-Iodo-7-ethyl-7H-imidazo[4,5-c]pyridazine

To a mixture of 4-chloro-7-ethyl-7H-imidazo[4,5-c]pyridazine (Preparation 17, 7.80 g, 42.7 mmol) in hydroiodic acid (130 mL, 55% aq) was added sodium iodide (12.8 g, 85.4 mmol) and the mixture was heated to 70° C. for 1 hour. A yellow precipitate formed almost immediately. The pH of the mixture was adjusted to pH 7 with solid NaHCO$_3$ (vicious gas evolution). The resulting aqueous layer was extracted with DCM to give the title compound as yellow solid, which turns green on standing (9.90 g, 85%).

$^1$H NMR (400 MHz, CDCl$_3$): δ ppm 1.66 (t, 3H), 4.53 (q, 2H), 8.33 (d, 1H), 9.40 (s, 1H).

Preparation 16

4-Chloro-7-cyclopropyl-7H-imidazo[4,5-c]pyridazine

A mixture of 5-chloro-N$^3$-cyclopropylpyridazine-3,4-diamine (Preparation 20, 10.0 g, 54 mmol) and triethylorthoformate (120 mL) were heated to reflux for 3 hours. The reaction mixture was concentrated in vacuo and the residue was purified by silica gel column chromatography eluting with DCM:MeOH 98:2 to afford the title compound as a brown solid (5 g, 48%).

$^1$H NMR (400 MHz, DMSO-d$_6$): δ ppm 1.05-1.30 (m, 4H), 3.75-3.85 (m, 1H), 8.88 (s, 1H), 9.26 (s, 1H)
MS m/z 195 [M$^{35}$Cl+H]$^+$ Preparation 17

4-Chloro-7-ethyl-7H-imidazo[4,5-c]pyridazine

A mixture of 5-chloro-N$^3$-ethyl-pyridazine-3,4-diamine (Preparation 18, 10.0 g, 58 mmol) and triethylorthoformate (60 mL) were heated to reflux for 4 hours. The reaction mixture was concentrated in vacuo and the residue was dissolved in EtOAc (50 mL) and filtered. The filter cake was washed with EtOAc and then the organic layers were washed with saturated brine solution, dried over Na$_2$SO$_4$ and concentrated in vacuo to afford the title compound as a yellow solid (4.8 g, 45%). Taken on directly to the next step.

Preparation 18

5-Chloro-N$^3$-ethylpyridazine-3,4-diamine

A mixture of 3,5-(dichloropyridazin-4-yl)amine (Preparation 21, 15 g, 92 mmol) and anhydrous ethylamine (50 mL) was heated to 120° C. for 48 hours in a sealed tube. The reaction mixture was cooled to room temperature, and then added to a mixture of water (500 mL) and EtOAc (50 mL). The resulting precipitate was separated by filtration and the filter cake was washed with TBME, and dried under vacuum to afford the title compound as off-white solid (8.1 g, 51%).

$^1$H NMR (400 MHz, DMSO-d$_6$): δ ppm 1.18 (t, 3H), 3.41 (q, 2H), 6.08-6.11 (m, 3H), 8.09 (s, 1H).

Preparation 19

5-Chloro-N$^3$-isopropylpyridazine-3,4-diamine

A solution of 3,5-dichloropyridazin-4-amine (Preparation 21, 4 g, 14.4 mmol) in isopropylamine (16 mL) and water (5 mL) was heated to 150° C. for 16 hours. The reaction was allowed to cool, water (20 mL) was added and the reaction extracted into EtOAc (3×30 mL). The combined extracts were concentrated in vacuo to afford the title compound.

$^1$H NMR (400 MHz, CDCl$_3$): δ ppm 1.24 (d, 6H), 4.38 (m, 1H), 4.80 (s, 1H), 4.97 (s, 2H), 8.27 (s, 1H).

Preparation 20

5-Chloro-N$^3$-cyclopropylpyridazine-3,4-diamine 3,5-Dichloropyridazin-4-amine (Preparation 21, 5.12 g, 31.2 mmol) was added to cyclopropylamine (37.0 g, 650 mmol) in a stainless steel sealed container (100 mL capacity), to afford a homogenous solution. The mixture was heated for 12 hours at 120° C. before cooling to room temperature and evaporating in vacuo. The residue was dissolved in EtOAc (150 mL) with sonication and stirring. The EtOAc solution was washed with 10% aqueous potassium carbonate solution (2×200 mL), dried over anhydrous MgSO$_4$, then filtered and evaporated in vacuo. The mixture was redissolved in DCM and purified using silica gel column chromatography eluting with DCM (100 mL), then EtOAc (150 mL) to afford the title compound as a light orange solid (4.2 g, 73% yield).

$^1$H NMR (400 MHz, DMSO-d$_6$): δ ppm 0.2-0.5 (m, 2H), 0.38-0.40 (m, 2H), 2.85-2.95 (m, 1H), 5.75 (b s, 2H), 6.0-6.05 (b s, 1H), 7.80 (s, 1H).

Preparation 21

3,5-Dichloropyridazin-4-amine

A mixture of 3,4,5-trichloropyridazine (Preparation 22, 500 mg, 2.73 mmole) in EtOH (5.5 mL) and NH$_4$OH (5.5 mL) was heated under microwave irradiation 120° C. for 25 minutes. The reaction was concentrated in vacuo and purified using silica gel column chromatography eluting with acetone:dichloromethane (0-15% acetone) to afford the title compound (163 mg, 36%).

$^1$H NMR (400 MHz, CDCl$_3$): δ ppm 5.11 (br s, 2H), 8.74 (s, 1H).
MS m/z 164 [M$^{35}$Cl$^{35}$Cl+H]

Preparation 22

3,4,5-Trichloropyridazine 4,5-Dichloropyridazin-3(2H)-one (10.0 g, 60.6 mmole) in POCl$_3$ (60 mL, 642 mmole) was stirred at 110° C. for 18 hours. The reaction was concentrated in vacuo azeotroping with toluene. EtOAc (200 mL) and water were added to the resulting residue and the organic layer was washed with water and brine, dried over MgSO$_4$ and concentrated in vacuo to afford the title compound as an off white solid (10 g, 90%).

$^1$H NMR (400 MHz, CDCl$_3$): δ ppm 9.10 (d, 1H).

Preparation 23

6-Methoxy-2-methyl-5-(4,4,5,5-tetramethyl-1,3,2-dioxaborolan-2-yl)isoindolin-1-one A solution of 5-chloro-6-methoxy-2-methylisoindolin-1-one (Preparation 24, 500 mg, 2.36 mmol), 4,4,4',4',5,5,5',5'-octamethyl-2,2'-bi(1,3,2-dioxaborolane) (780 mg, 3.07 mmol) and potassium acetate (463 mg, 4.72 mmol) in 1,4-dioxane (15 mL) at room temperature was degassed with nitrogen. After 1 hour tricyclohexylphosphine (165 mg, 0.590 mmol) and tris(dibenzylideneacetone)dipalladium(0) (108 mg, 0.150 mmol) were sequentially added and the reaction heated to 110° C. After 18 hours the reaction was cooled to room temperature and the solution filtered through celite, washed with ethyl acetate (3×50 mL) and concentrated in vacuo. The residue was purified using silica gel column chromatography eluting with 20-100% ethyl acetate in heptanes followed by tritiurated in 50% EtOAc in heptanes to afford the title compound as a colourless solid (93 mg, 13%).

$^1$H NMR (400 MHz, CDCl$_3$): δ ppm 1.37 (s, 12H), 3.20 (s, 3H), 3.89 (s, 3H), 4.29 (s, 2H), 7.29 (s, 1H), 7.69 (s, 1H).
MS m/z 222 [M+H]$^+$ boronic acid.

Preparation 24

5-Chloro-6-methoxy-2-methylisoindol-1-one

To a suspension of 5-chloro-6-methoxyisoindolin-1-one (Preparation 25, 105 mg, 0.53 mmol) in THF (3 mL) at 0° C. was added NaH (60% dispersion in oil, 22 mg, 0.55 mmol) and the reaction was stirred at this temperature for 10 minutes followed by room temperature for 10 minutes. The reaction was cooled back to 0° C., iodomethane (38 μL, 0.61 mmol) was added and the reaction was stirred warming to room temperature for 18 hours. The reaction was quenched by the addition of water (few drops) and partitioned between EtOAc (40 mL) and aqueous ammonium chloride solution (30 mL). The organic layer was collected, dried over Na$_2$SO$_4$ and concentrated in vacuo to afford the title compound as a beige powder (102 mg, 91%).

$^1$H NMR (400 MHz, CDCl$_3$): δ ppm 3.19 (s, 3H), 3.96 (s, 3H), 4.30 (s, 2H), 7.37 (s, 1H), 7.45 (s, 1H).
MS m/z 212 [M$^{35}$Cl+H]

Preparation 25

5-Chloro-6-methoxyisoindolin-1-one

Methyl 4-chloro-2-cyano-5-methoxybenzoate (Preparation 26, 180 mg, 0.798 mmol) was dissolved in MeOH (20 mL) and EtOAc (5 mL) by gentle heating. 880 aqueous ammonia (0.5 mL) was added and the reaction hydrogenated over Raney Nickel (150 mg) at 45 psi for 5 hours. The reaction was filtered through celite and concentrated in vacuo. The residue was purified using silica gel column chromatography eluting with 0.5-2% MeOH in DCM to afford the title compound as an off white powder (105 mg, 67%).

$^1$H NMR (400 MHz, CDCl$_3$): δ ppm 3.97 (s, 3H), 4.39 (s, 2H), 6.46 (br s, 1H), 7.40 (s, 1H), 7.50 (s, 1H).
MS m/z 198 [M$^{35}$Cl+H]$^+$ Preparation 26

Methyl 4-chloro-2-cyano-5-methoxybenzoate

Methyl 2-bromo-4-chloro-5-methoxybenzoate (Preparation 27, 1.00 g, 3.58 mmol) and copper cyanide (0.39 g, 4.29 mmol) were dissolved in DMF (15 mL) and heated to 150° C. for 2 hours. After cooling to room temperature the reaction was diluted with EtOAc (30 mL) and stirred for 10 minutes. The resulting suspension was filtered, the filtrate was washed with 1M aqueous NaOH (2×50 mL), brine (50 mL), dried over MgSO$_4$ and concentrated in vacuo. The residue was purified using silica gel column chromatography eluting with 20% EtOAc in heptanes followed by recrystallisation from EtOAc/Heptanes to afford the title compound as a colourless solid (320 mg, 40%).

$^1$H NMR (400 MHz, CDCl$_3$): δ ppm 4.01 (s, 6H), 7.64 (s, 1H), 7.77 (s, 1H).

Preparation 27

Methyl 2-bromo-4-chloro-5-methoxybenzoate

To a suspension of methyl 4-chloro-3-methoxybenzoate (Preparation 41, 2.61 g, 13.0 mmol) in AcOH (10 mL) and water (10 mL) was added bromine (1 mL, 20 mmol) dropwise over 10 minutes. The reaction was heated to 60° C. for 1 hour. The reaction was cooled to room temperature, and the resulting precipitate filtered, washed with water (2×20 mL) and dried to afford the title compound as a yellow solid (3.60 g, 99%).

$^1$H NMR (400 MHz, CDCl$_3$): δ ppm 3.93 (s, 3H), 3.94 (s, 3H), 7.38 (s, 1H), 7.66 (s, 1H).

Preparation 28

2',6-Difluoro-N-methyl-5'-(4,4,5,5-tetramethyl-1,3,2-dioxaborolan-2-yl)biphenyl-3-carboxamide The title compound was prepared according to the method described for Preparation 3 using 5'-bromo-2',6-difluoro-N-methylbiphenyl-3-carboxamide (Preparation 40) at 100° C. for 15 hours. The reaction was cooled, diluted with water and extracted with EtOAc. The organic layer was collected, washed with water, brine, dried over Na$_2$SO$_4$ and concentrated in vacuo. The residue was purified using silica gel column chromatography eluting with 25-30% EtOAc in hexane to afford the title compound (4.89 g, 87%).

$^1$H NMR (400 MHz, CDCl$_3$): δ ppm 1.33 (s, 12H), 3.00 (d, 3H), 4.11 (q, 1H), 7.13-7.25 (m, 2H), 7.77-7.85 (m, 4H).

Preparation 29

Methyl-3-methoxy-4-(4,4,5,5-tetramethyl-1,3,2-dioxaborolan-2-yl)benzoate

The title compound was prepared according to the method described for Preparation 3 using methyl-4-bromo-3-methoxybenzoate (500 mg, 2.04 mmol) at 100° C. for 6 hours. The reaction was cooled, concentrated in vacuo and the residue was purified using silica gel column chromatography eluting with 25-50% EtOAc in heptanes to afford a colourless gum.

$^1$H NMR (400 MHz, CDCl$_3$): δ ppm 1.34 (s, 12H), 3.88 (s, 3H), 3.92 (s, 3H), 7.50 (d, 1H), 7.58-7.61 (dd, 1H), 7.70 (d, 1H).
MS m/z 293 [M+H]$^+$ Preparation 30

2'-Fluoro-5'-(4,4,5,5-tetramethyl-1,3,2-dioxaborolan-2-yl)biphenyl-4-carboxamide The title compound was prepared according to the method described for Preparation 3 using 5'-bromo-2'-fluorobiphenyl-4-carboxamide (Preparation 39) in DMSO at 85° C. under microwave irradiation for 20 minutes. Further bispinacolato diboron (66 mg, 0.261 mmol), potassium acetate (41 mg, 0.41 mmol) and [1,1'-bis(diphenylphosphino)ferrocene]dichloropalladium (II) complex with dichloromethane (5 mg, 0.06 mmol) were added and the reaction continued heating at 80° C. under microwave irradiation for 10 minutes. The reaction was cooled, concentrated in vacuo and purified using silica gel column chromatography eluting with 0-60% EtOAc in Heptane to afford a yellow solid (170 mg, 81%).

¹H NMR (400 MHz, CDCl₃): δ ppm 1.36 (s, 12H), 1.54-1.62 (m, 2H), 7.15-7.21 (m, 1H), 7.66-7.70 (m, 2H), 7.79-7.85 (m, 1H), 7.89 (m, 3H).

Preparation 31

2-[3-(4,4,5,5-Tetramethyl-[1,3,2]dioxaborolan-2-yl) phenyl]-2,3-dihydro-1H-1,3-diaza-2-boraphenalene The title compound was prepared according to the method described for Preparation 3 using 2-(3-bromophenyl)-2,3-dihydro-1H-1,3-diaza-2-boraphenalene (Preparation 38), tricyclohexylphosphine and bis(dibenzylideneacetone) dipalladium at reflux for 16 hours. The reaction mixture was cooled to room temperature then concentrated in vacuo. The residue was purified by silica gel column chromatography eluting with petroleum ether:EtOAc 5:1 to afford a yellow solid (16 g, 61%).

¹H NMR (400 MHz, CDCl₃): δ ppm 1.37 (s, 12H), 6.12 (d, 2H), 6.43 (d, 2H), 7.04-7.16 (m, 4H), 7.41-7.42 (m, 1H), 7.72-7.77 (m, 1H), 7.89-7.90 (m, 1H), 8.09 (s, 1H).

Preparation 32

6-(4,4,5,5-Tetramethyl-1,3,2-dioxaborolan-2-yl)-2,3-dihydro-1H-isoindol-1-one

A solution of methyl 2-(aminomethyl)-5-(4,4,5,5-tetramethyl-1,3,2-dioxaborolan-2-yl)benzoate (Preparation 33, 45 g, 0.15 mmol) in MeOH (0.5 L) was stirred at reflux for 3 hours. The reaction was cooled, concentrated in vacuo and the residue washed with water (2×50 mL) and methanol (2×100 mL) to afford the title compound (35 g, 90%).

¹H NMR (400 MHz, DMSO-d₆): δ ppm 1.31 (s, 12H), 4.40 (s, 2H), 7.60 (d, 1H), 7.88 (d, 1H), 7.93 (s, 1H), 8.59 (br s, 1H).

Preparation 33

Methyl 2-(aminomethyl)-5-(4,4,5,5-tetramethyl-1,3,2-dioxaborolan-2-yl)benzoate

A suspension of methyl 2-(bromomethyl)-5-(4,4,5,5-tetramethyl-1,3,2-dioxaborolan-2-yl)benzoate (Preparation 36, 60 g, 0.17 mmol) in MeOH (0.5 L) was purged with ammonia. Upon completion of the reaction the mixture was concentrated in vacuo. The residue was diluted with EtOAc (300 mL), washed with brine (500 mL) and concentrated in vacuo to afford the title compound as a brown solid (45 g, 91%) that was taken on directly to the next step.

Preparation 34

2-Methyl-6-(4,4,5,5-tetramethyl-1,3,2-dioxaborolan-2-yl)-2,3-dihydro-1H-isoindol-1-one A solution of methyl 2-[(methylamino)methyl]-5-(4,4,5,5-tetramethyl-1,3,2-dioxaborolan-2-yl)benzoate (Preparation 35, 40 g, 0.14 mol) in acetonitrile (0.5 L) was heated to reflux for 2 hours. The reaction was cooled and concentrated in vacuo. The residue was diluted with EtOAc (500 mL), washed with brine (2×100 mL) and concentrated in vacuo to afford the title compound as a grey solid (35 g, 99%).

¹H NMR (400 MHz, CDCl₃): δ ppm 1.35 (s, 12H), 3.20 (s, 3H), 4.38 (s, 2H), 7.42 (d, 1H), 7.90 (d, 1H), 8.30 (s, 1H). MS m/z 274 [M+H]⁺

Preparation 35

Methyl 2-[(methylamino)methyl]-5-(4,4,5,5-tetramethyl-1,3,2-dioxaborolan-2-yl)benzoate To a solution of methyl 2-(bromomethyl)-5-(4,4,5,5-tetramethyl-1,3,2-dioxaborolan-2-yl)benzoate (Preparation 36, 56 g, 0.16 mol) in MeOH (0.5 L) was added methylamine (21 g, 0.6 mol) followed by triethylamine (73 g, 0.68 mol) and the reaction was heated at reflux for 2 hours. The reaction was cooled and concentrated in vacuo. The residue was taken up in EtOAc (1 L) and filtered. The filtrate was concentrated in vacuo and the resulting solid washed with ether (500 mL) to afford the title compound (40 g, 80%) that was taken directly on to the next step.

Preparation 36

Methyl 2-(bromomethyl)-5-(4,4,5,5-tetramethyl-1,3,2-dioxaborolan-2-yl)benzoate

To a solution of methyl 2-methyl-5-(4,4,5,5-tetramethyl-1,3,2-dioxaborolan-2-yl)benzoate (Preparation 37, 60 g, 0.22 mol) and NBS (71 g, 0.40 mol) in carbon tetrachloride (1 L) was added benzoyl peroxide (5 g), and the reaction heated to 80° C. for 2 hours. The reaction was cooled and filtered. The filtrate was collected, washed with water, the organic layer dried over Na₂SO₄ and concentrated in vacuo to afford the title compound (56 g, 72%) that was taken directly on to the next step.

Preparation 37

Methyl 2-methyl-5-(4,4,5,5-tetramethyl-1,3,2-dioxaborolan-2-yl)benzoate

To a solution of methyl 5-iodo-2-methylbenzoate (Preparation 42, 69 g, 0.25 mol) in DMF (800 mL) was added bispinacolatodiboron (100 g, 0.40 mol) and potassium acetate (92 g, 0.93 mol) followed by degassing with nitrogen. [1,1'-bis(diphenylphosphino)ferrocene]dichloropalladium (II) complex with dichloromethane (6 g) was added and the reaction heated to 100° C. for 18 hours. The reaction was cooled and filtered through celite, washing through with EtOAc (3×1 L). The filtrates were combined, washed with brine (3×500 mL), dried over Na₂SO₄ and concentrated in vacuo. The residue was washed with petroleum ether (2×500 mL), filtered and dried to afford the title compound as a yellow powder (60 g, 87%) that was taken directly on to the next step.

Preparation 38

2-(3-Bromophenyl)-2,3-dihydro-1H-1,3-diaza-2-boraphenalene

A solution of 3-bromobenzeneboronic acid (20 g, 0.1 mol) and naphthalene-1,8-diamine (17.3 g, 0.11 mol) in anhydrous toluene (600 mL) was heated to reflux for 16 hours. The reaction mixture was cooled to room temperature, and concentrated in vacuo. The residue was purified by silica gel column chromatography eluting with petroleum ether:EtOAc 5:1 to afford the title compound as a grey solid (23 g, 54%).

¹H NMR (400 MHz, CDCl₃): δ ppm 5.91 (s, 2H), 6.35 (d, 2H), 7.00 (d, 2H), 7.06-7.09 (m, 2H), 7.24-7.26 (m, 1H), 7.47-7.55 (m, 2H), 7.69 (s, 1H).

Preparation 39

5'-Bromo-2'-fluorobiphenyl-4-carboxamide

To a solution of 4-carbamoylbenzeneboronic acid (204 mg, 1.2 mmol) and 1-fluoro-2-iodo-4-bromobenzene (361 mg, 1.2 mmol) in dioxane (3.5 mL) was added [1,1'-bis(diphenylphosphino)ferrocene]dichloropalladium (II) complex with dichloromethane (34 mg, 0.042 mmol) followed by a solution of sodium carbonate (382 mg) in water (1 mL). The reaction was heated to 90° C. under microwave irradiation for 20 minutes. The reaction was cooled, diluted with EtOAc, dried over sodium sulphate and concentrated in vacuo. The residue was purified using silica gel column chromatography eluting with 0-50% EtOAc in Heptanes to afford the title compound as an off-white solid (180 mg, 51%).
¹H NMR (400 MHz, CDCl₃): δ ppm 2.38 (s, 2H), 6.99 (m, 2H), 7.38 (m, 1H), 7.45-7.57 (m, 2H), 7.76-7.97 (m, 2H).

Preparation 40

5'-Bromo-2',6-difluoro-N-methylbiphenyl-3-carboxamide

To a solution of 3-bromo-6-fluoro-iodobenzene (7.29 g, 36.5 mmol) in dioxane (175 mL) was added 2-fluoro-5-(methylcarbamoyl)benzeneboronic acid (10 g, 33.2 mmol) followed by a 1M Na₂CO₃ aqueous solution in water (166 mL). The mixture was degassed before the addition of tetrakis(triphenylphosphine)palladium(0) (1.92 g, 1.66 mmol). The reaction was heated to 110° C. for 16 hours before cooling. The reaction was filtered, concentrated in vacuo and purified using silica gel column chromatography eluting with 60% EtOAc in hexanes to afford the title compound.
¹H NMR (400 MHz, CDCl₃): δ ppm 3.00 (s, 3H), 6.12 (brs, 1H), 7.06 (m, 1H), 7.23 (m, 1H), 7.50 (m, 2H), 7.79 (m, 2H).
MS m/z 326 [M⁷⁹Br+H]⁺

Preparation 41

Methyl 4-chloro-3-methoxybenzoate

4-Chloro-3-methoxybenzoic acid (2.5 g, 13 mmol) was dissolved in methanol (40 mL) followed by the addition of sulphuric acid (0.3 mL) and heated to reflux for 48 hours. The reaction was cooled and concentrated in vacuo. The residue was partitioned between EtOAc (15 mL) and water (15 mL), the organic layer was collected, washed with 1M aqueous NaOH (15 mL), dried over magnesium sulphate and concentrated in vacuo to afford the title compound (2.61 g, 100%).
¹H NMR (400 MHz, CDCl₃): δ ppm 3.86 (s, 3H), 3.89 (s, 3H), 7.34 (d, 1H), 7.48-7.52 (m, 2H).

Preparation 42

Methyl 5-iodo-2-methylbenzoate

To a solution of 5-iodo-2-methylbenzoic acid (86 g, 0.57 mol) in MeOH (0.5 L) was added thionyl chloride (74 g, 0.62 mol) dropwise at 0° C., and after complete addition the reaction was heated to reflux for 2 hours. The reaction was cooled, concentrated in vacuo, diluted with water and extracted into EtOAc (2×300 mL). The organic layers were combined, washed with brine, dried over Na₂SO₄ and concentrated in vacuo to afford the title compound that was taken directly on to the next step (69 g, 73%).

Assay Methods

Cell Line Construction and Maintenance

Human Embryonic Kidney (HEK) cells were transfected with a GABRA2-GABRB2-GABRG2 construct using standard techniques. Cells stably expressing the GABRA2-GABRB2-GABRG2 constructs were identified by their resistance to Geneticin G-418 (320 µg/ml), Hygromycin (160 µg/ml) and Zeocin (40 µg/ml). Clones were screened for expression using the BD Pathway 855 imaging system (BD Biosciences, Rockville, Md., USA) and QPatch automated electrophysiology platform (Sophion, Copenhagen, Denmark).

Cell Culture

HEK cells stably transfected with GABRA2-GABRB2-GABRG2 were maintained in MEM medium with Earle's salts, 10% FBS, 1× L-Glutamax, 1% mM Non-essential Amino Acids (MEM) and 1 mM sodium pyruvate, with Geneticin G-418 (320 µg/ml), Hygromycin (160 µg/ml) and Zeocin (40 µg/ml), in an incubator at 37° C. with a humidified atmosphere of 5% CO₂. For QPatch electrophysiology testing, cells were harvested from flasks by enzymatic dissociation and resuspended in serum-free medium. Cells were typically used for electrophysiological experiments within 24 to 72 hours after splitting.

Binding Assay

The affinity of the test compounds was determined by radioligand competition binding assay, using the known compound [3H]Ro-15-1788 (Flumazenil) (Perkin Elmer, 85.4 Ci/mmol) and the human recombinant GABA A receptor containing the alpha2, beta2, and gamma3 subunits.

Membranes were prepared from HEK cells expressing hGABA A alpha2beta2-gamma3 receptor, and validated to ascertain protein concentration, receptor expression and to determine the Kd of the flumazenil as well as the Ki of a standard set of compounds before being used to test new compounds.

The assay was carried out in 96 well plates; testing compounds using a 10 point semi-log dilution range from 19 uM top concentration. 100 ul of radioligand and 100 ul of membrane in 50 mM Tris-HCl and 0.05% F127 with 1 ul of test compound was incubated for 2 hours to allow the reaction to achieve equilibrium, and then harvested onto filter plates, dried and counted on a TopCount NXT. The data was analysed, and the Ki values were presented as the geometric mean of at least two replicates.

Electrophysiological Recording

Cell suspension containing HEK cells expressing GABRA2-GABRB2-GABRG2 was placed on the QPatch instrument in serum-free medium into the instrument's cell stirrer. The instrument washed the cells once using extracellular buffer and then dispensed them into the QPlate HT measurement plate at a concentration of 3-4e6/ml. Extracellular solution was of the following composition: 137 mM NaCl, 1.8 mM CaCl₂, 4 mM KCl, 1 mM MgCl₂, 10 mM glucose, and 10 mM HEPES, pH 7.4 with NaOH, 300-310 mOsm/kg. The internal side of the QPlate measurement plate was filled with intracellular solution of the following composition: 90 mM KCl, 50 mM KF, 1 mM MgCl₂, 10 mM HEPES, 11 mM EGTA, and 2 mM Mg-ATP, pH 7.35, with KOH, 295-305 mOsm/kg. All recordings were made at room temperature (22-24° C.).

GABRA2-GABRB2-GABRG2 chloride currents in HEK cells were measured using the whole-cell configuration of the patch-clamp technique (Hamill et al., 1981). Current records were acquired at 1 KHz and filtered at 0.3 KHz using the Bessel filter. Series resistance compensation was set to 80% in the QPatch software.

All compounds were dissolved in dimethyl sulfoxide to make 30 mM or 10 mM stock solutions, which were then diluted to 1000 times the desired final concentration in dimethyl sulfoxide. These were diluted into extracellular solution to attain the final concentrations desired. The final concentration of dimethyl sulfoxide (<0.1% dimethyl sulfoxide) was found to have no significant effect on GABRA2-GABRB2-GABRG2 chloride currents. This concentration of dimethyl sulfoxide was present in all samples.

Currents were recorded at −60 mV, using an approximately EC10 concentration of gamma-aminobutyric acid (GABA). This dose of gamma-aminobutyric acid was applied for 6 seconds and washed off using extracellular buffer as an unrecorded application using the pipetting system of the QPatch instrument. The same dose of gamma-aminobutyric acid was then applied for 9 seconds, then the test compound was co-applied with this dose of gamma-aminobutyric acid for 15 seconds, and washed off using the extracellular solution using the pipetting system of the QPatch instrument.

Compound effect (% enhancement of gamma-aminobutyric acid current) was calculated using the following formula:

[((peak modulator current amplitude−leak)−(GABA current amplitude−leak))/(GABA current amplitude−leak)]*100, where 'leak' is leak current at −60 mV, 'peak modulator current amplitude' is the current elicited by co-application of gamma-aminobutyric acid and test compound, and 'GABA current amplitude' is the current elicited by application of gamma-aminobutyric acid alone.

The ability of the compounds of the formula (I) to modulate the GABA channels expressing the α1 subunit (or GABRA1) can also be measured using an assay analogous to that described above but replacing the GABRA2-GABRB2-GABRG2 gene construct with the GABRA1-GABRB3-GABRG2 gene construct. All other conditions remain the same including the same cell line and conditions for cell growth. The % enhancement values generated in the assay using the GABRA1-GABRB3-GABRG2 construct can be compared to the results generated using the GABRA2-GABRB2-GABRG2 construct to determine the selectivity of a given compound.

Results

| Example | GABA-α2 Ki (nM) | α1 PAM (%) | α2 PAM (%) |
|---|---|---|---|
| 1 | 6.6 | −27 | 96 |
| 2 | 6.4 | 12 | 106 |
| 3 | 12.8 | −30 | 47 |
| 4 | 23.2 | −10 | 30 |
| 5 | 21.7 | −29 | 43 |
| 6 | 81.8 | −61 | 10 |
| 7 | 30.9 | | 47 |
| 8 | 29.0 | | |
| 9 | 6.8 | −11 | 17 |
| 10 | 54.7 | −12 | 36 |
| 11 | 20.5 | | 60 |

-continued

| Example | GABA-α2 Ki (nM) | α1 PAM (%) | α2 PAM (%) |
|---|---|---|---|
| 12 | 10.7 | | 48 |
| 13 | 71.6 | −14 | 13 |
| 14 | 7.5 | −55 | 11 |
| 15 | 20.3 | −34 | 40 |
| 16 | 6.7 | −41 | 21 |
| 17 | 52.8 | | |
| 18 | 19.3 | | |
| 19 | 51.0 | 14 | 66 |
| 20 | 224.3 | | |
| 21 | 6.3 | −29 | 33 |
| 22 | 81.2 | −1 | 23 |
| 23 | 340.4 | | |

The invention claimed is:

1. A compound according to formula (I)

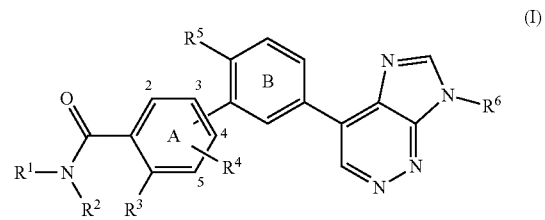

wherein
$R^1$ is selected from H and $(C_1-C_3)$alkyl:
$R^2$ is selected from H and $(C_1-C_3)$alkyl and $R^3$ is H; or
$R^2$ and $R^3$ together are —$CH_2$—;
$R^4$ is selected from H, F and $OCH_3$;
$R^5$ is selected from H and F; and
$R^6$ is selected from $(C_2-C_4)$alkyl, $(C_3-C_5)$cycloalkyl and methyl-substituted $(C_3-C_5)$cycloalkyl,
and wherein
ring B is attached to ring A at any one of positions 3, 4 and 5; and
$R^4$ is attached to ring A at any one of positions 2, 3, 4 and 5, provided that $R^4$ and ring B cannot both be attached to ring A at the same position,
or a pharmaceutically acceptable salt thereof.

2. The compound of claim 1 according to formula ($I^4$)

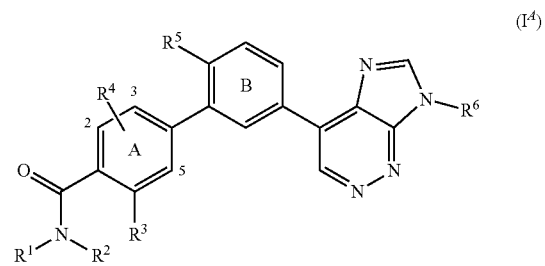

wherein
$R^1$, $R^2$, $R^3$, $R^4$, $R^5$ and $R^6$ are as defined in claim 1, and wherein
$R^4$ is attached to ring A at any one of positions 2, 3 and 5,
or a pharmaceutically acceptable salt thereof.

3. The compound of claim 1 according to formula ($I^B$)

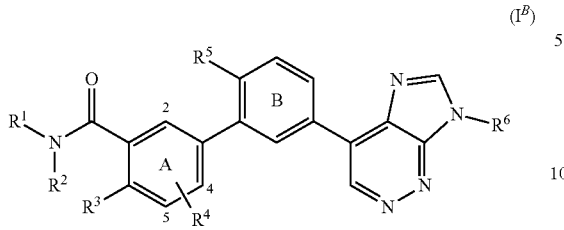

(I$^B$)

wherein
$R^1$, $R^2$, $R^3$, $R^4$, $R^5$ and $R^6$ are as defined in claim 1,
and wherein
$R^4$ is attached to ring A at any one of positions 2, 4 and 5,
or a pharmaceutically acceptable salt thereof.

4. The compound according to claim 1 wherein $R^4$ is selected from H and OCH$_3$, or a pharmaceutically acceptable salt thereof.

5. The compound according to claim 1 wherein $R^5$ is F, or a pharmaceutically acceptable salt thereof.

6. The compound according to claim 1 selected from:
5-[5-(7-ethyl-7H-imidazo[4,5-c]pyridazin-4-yl)-2-fluorophenyl]-6-methoxy-2-methyl-2,3-dihydro-isoindol-1-one,
5-[2-fluoro-5-(7-isopropyl-7H-imidazo[4,5-c]pyridazin-4-yl)-phenyl]-2-methyl-2,3-dihydro-isoindol-1-one,
5-[5-(7-ethyl-7H-imidazo[4,5-c]pyridazin-4-yl)-2-fluorophenyl]-2-methyl-2,3-dihydro-isoindol-1-one,
5'-(7-ethyl-7H-imidazo[4,5-c]pyridazin-4-yl)-2'-fluorobiphenyl-3-carboxamide,
6-[5-(7-ethyl-7H-imidazo[4,5-c]pyridazin-4-yl)-2-fluorophenyl]-2-methyl-2,3-dihydro-isoindol-1-one, and
5'-(7-ethyl-7H-imidazo[4,5-c]pyridazin-4-yl)-5,2'-difluoro-N-methyl-biphenyl-3-carboxamide,
or a pharmaceutically acceptable salt thereof.

7. A pharmaceutical composition comprising a compound according to claim 1 and a pharmaceutically acceptable excipient.

8. A method for the palliative treatment of pain comprising administration to a subject in need of such treatment an effective amount of a compound according to claim 1.

9. A combination for the treatment of pain comprising a compound according to claim 1 and a second pharmaceutically active agent.

* * * * *